US011713458B2

(12) United States Patent
Nawrath et al.

(10) Patent No.: US 11,713,458 B2
(45) Date of Patent: Aug. 1, 2023

(54) MEANS AND METHODS FOR MODIFYING MULTIPLE ALLELES

(71) Applicant: Octapharma AG, Lachen (CH)

(72) Inventors: Karina Nawrath, Lachen (CH); Janine Guendel, Lachen (CH); Sven Bahrke, Lachen (CH); Lars Stoeckl, Lachen (CH); Steffen Goletz, Lachen (CH)

(73) Assignee: Octapharma AG, Lachen (CH)

( * ) Notice: Subject to any disclaimer, the term of this patent is extended or adjusted under 35 U.S.C. 154(b) by 1069 days.

(21) Appl. No.: 16/311,561

(22) PCT Filed: Jun. 20, 2017

(86) PCT No.: PCT/EP2017/065010
§ 371 (c)(1),
(2) Date: Dec. 19, 2018

(87) PCT Pub. No.: WO2017/220527
PCT Pub. Date: Dec. 28, 2017

(65) Prior Publication Data

US 2019/0185848 A1 Jun. 20, 2019

(30) Foreign Application Priority Data

Jun. 20, 2016 (EP) .................................... 16001385
Oct. 7, 2016 (LU) ......................................... 93251

(51) Int. Cl.
*C12N 15/11* (2006.01)
*C12N 9/22* (2006.01)
*C12N 9/64* (2006.01)
*C12N 15/10* (2006.01)
*C12P 21/00* (2006.01)
*C12N 15/113* (2010.01)

(52) U.S. Cl.
CPC ................ *C12N 15/11* (2013.01); *C12N 9/22* (2013.01); *C12N 9/6437* (2013.01); *C12N 15/102* (2013.01); *C12P 21/005* (2013.01); *C12Y 304/21021* (2013.01); *C12N 15/1137* (2013.01); *C12N 2310/20* (2017.05); *C12N 2800/80* (2013.01)

(58) Field of Classification Search
CPC ....... C12N 15/11; C12N 9/22; C12N 2310/20
See application file for complete search history.

(56) References Cited

FOREIGN PATENT DOCUMENTS

| | | | | |
|---|---|---|---|---|
| WO | 2014165612 A2 | 10/2014 | | |
| WO | 2015010114 A1 | 1/2015 | | |
| WO | 2015138855 A1 | 9/2015 | | |
| WO | 2016081923 A2 | 5/2016 | | |
| WO | 2016091268 A2 | 6/2016 | | |
| WO | 2016100309 A1 | 6/2016 | | |
| WO | 2016196499 A1 | 12/2016 | | |
| WO | WO-2017047813 A1 * | 3/2017 | .......... | G01N 33/574 |

OTHER PUBLICATIONS

WO 2017/047813 A1 translation, downloaded Feb. 12, 2022 (Year: 2022).*

Butler, J.R., et al. (2016) "Silencing the porcine iGb3s gene does not affect Gala3Gal levels or measures of anticipated pig-to-human and pig-to-primate acute rejection", Xenotransplantation, 23:106-116.

Ikehara, Y., et al. (2006) "Apical Golgi localization of N,N-diacetyllactosediamine synthase, beta4GalNAc-T3, is responsible for LacdiNAc expression on gastric mucosa", Glycobiology, 16:777-785.

Ishino, Y., et al. (1987) "Nucleotide Sequence of the iap Gene, Responsible for Alkaline Phosphatase Isozyme Conversion in *Escherichia coli*, and Identification of the Gene Product", Journal of Bacteriology, 169:5429-5433.

Jinek, M., et al. (2012) "A Programmable Dual-RNA-Guided DNA Endonuclease in Adaptive Bacterial Immunity", Science, 337:816-821.

Stolfa, G., et al. (2016) "Using CRISPR-Cas9 to quantify the contributions of O-glycans, N-glycans and Glycosphingolipids to human leukocyte-endothelium adhesion", Scientific Reports, 6:30392.

"GRNA Synthesis Protocol" (2013) retrieved from https://www.addgene.org/static/cms/files/hCRISPR_gRNA_Synthesis.pdf, 1 page.

Uhler, R., et al. (2021) Glyco-engineered HEK 293-F cell lines for the production of therapeutic glycoproteins with human N-glycosylation and improved pharmacokinetics. Glycobiology, 1-14, doi: 10.1093/glycob/cwaa119.

* cited by examiner

*Primary Examiner* — Antonio Galisteo Gonzalez
(74) *Attorney, Agent, or Firm* — Kagan Binder, PLLC

(57) ABSTRACT

The present invention relates to a method of modifying at least one gene in a cell via CRISPR/Cas, wherein the at least one gene has at least three alleles. The present invention further relates to cells obtainable by the method of the invention. Additionally, the present invention provides a method of producing a protein in a cell obtainable by the method of modifying at least one gene of the invention. Moreover, the invention relates to proteins obtainable by the method of producing a protein and use thereof, for example in therapy.

11 Claims, 3 Drawing Sheets

Specification includes a Sequence Listing.

| | | F | oF | B | S | S1 | S2 | S3 | S4 | HB | M | G | G1 | G2 | G3 | G4 | tG | tG1 | tG2 | tG3 | tG4 | GN | GN 1 | GN 2 | GN 3 | GN 4 | tGN | tGN 1 | tGN 2 | tGN 3 | tGN 4 | A1 | A2 | A3 | A4 | Le$^x$ |
|---|---|---|---|---|---|---|---|---|---|---|---|---|---|---|---|---|---|---|---|---|---|---|---|---|---|---|---|---|---|---|---|---|---|---|---|---|
| FVII | GNT3/4-ko | 93 | 28 | 23 | 81 | 39 | 31 | 9 | 2 | 1 | 5 | 94 | 4 | 56 | 24 | 9 | 66 | 46 | 18 | 3 | 0 | 0 | 0 | 0 | 0 | 0 | 0 | 0 | 0 | 0 | 0 | 0 | 59 | 26 | 15 | 28 |
| FVII | GNT3-ko | 94 | 31 | 24 | 70 | 31 | 31 | 8 | 1 | 1 | 4 | 93 | 17 | 54 | 19 | 4 | 57 | 33 | 22 | 2 | 0 | 14 | 13 | 2 | 0 | 0 | 7 | 6 | 1 | 0 | 0 | 0 | 68 | 20 | 6 | 27 |
| FVII | GNT3-ko | 99 | 39 | 10 | 79 | 39 | 31 | 8 | 1 | 1 | 1 | 87 | 24 | 43 | 16 | 5 | 54 | 42 | 11 | 1 | 0 | 38 | 26 | 12 | 0 | 0 | 24 | 16 | 8 | 0 | 0 | 0 | 71 | 21 | 7 | 21 |
| FVII | Ref.* | 100 | 44 | 31 | 80 | 58 | 18 | 2 | 0 | 0 | 0 | 96 | 22 | 39 | 23 | 9 | 79 | 46 | 23 | 9 | 0 | 29 | 23 | 5 | 0 | 0 | 18 | 15 | 2 | 0 | 0 | 0 | 63 | 25 | 11 | 40 |
| FVII | ST6-oe+GNT3/4 ko | 98 | 7 | 27 | 100 | 5 | 59 | 29 | 7 | 0 | 0 | 100 | 0 | 55 | 35 | 10 | 17 | 16 | 1 | 0 | 0 | 0 | 0 | 0 | 0 | 0 | 0 | 0 | 0 | 0 | 0 | 0 | 53 | 29 | 18 | 7 |
| FVII | ST6-oe+GNT3/4 ko-P1215-G3 | 99 | 18 | 51 | 91 | 28 | 55 | 8 | 1 | 0 | 1 | 97 | 8 | 67 | 19 | 3 | 39 | 31 | 7 | 2 | 0 | 0 | 0 | 0 | 0 | 0 | 0 | 0 | 0 | 0 | 0 | 0 | 73 | 18 | 7 | 18 |
| FVII | ST6-oe | 100 | 24 | 17 | 94 | 34 | 56 | 4 | 0 | 0 | 0 | 85 | 28 | 41 | 12 | 4 | 37 | 28 | 8 | 1 | 0 | 46 | 33 | 13 | 0 | 0 | 14 | 12 | 2 | 0 | 0 | 2 | 77 | 15 | 6 | 16 |

Figure 1:
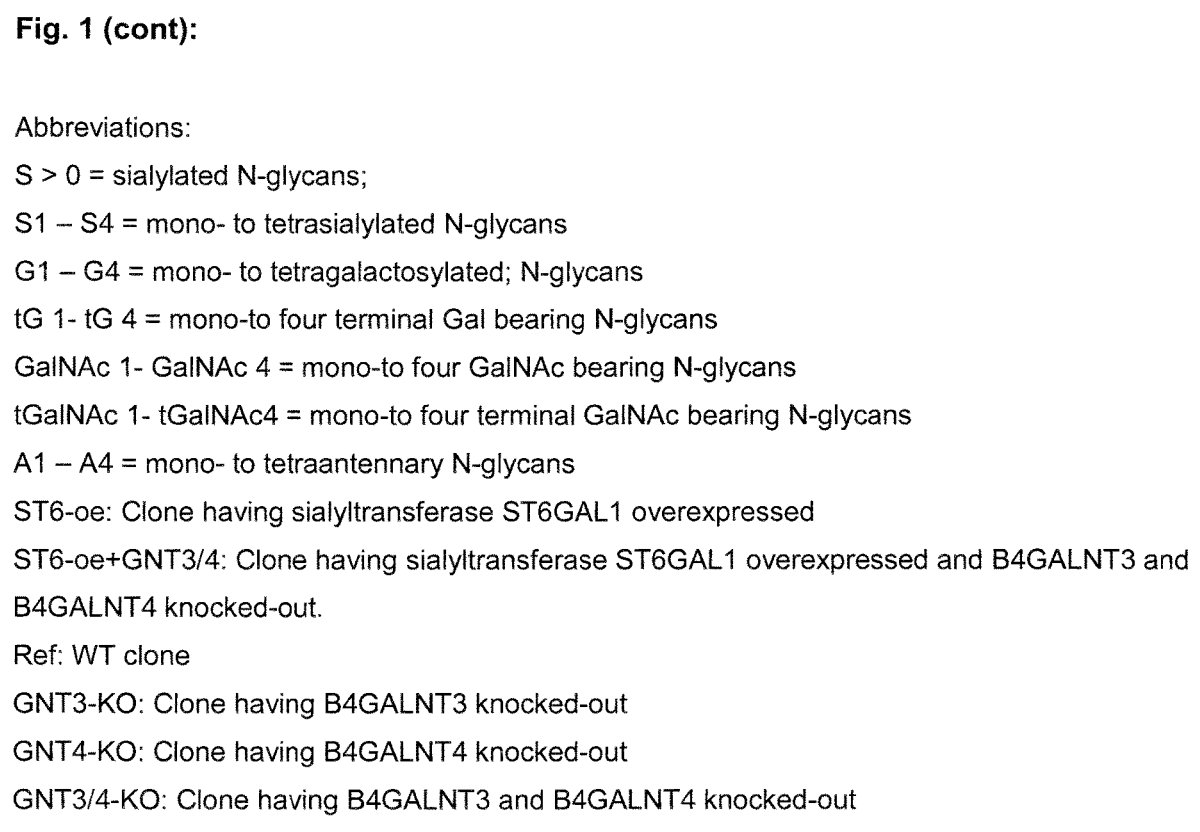

Abbreviations:

S > 0 = sialylated N-glycans;

S1 – S4 = mono- to tetrasialylated N-glycans

G1 – G4 = mono- to tetragalactosylated; N-glycans tG 1- tG 4 = mono-to four terminal Gal bearing N-glycans GalNAc 1- GalNAc 4 = mono-to four GalNAc bearing N-glycans tGalNAc 1- tGalNAc4 = mono-to four terminal GalNAc bearing N-glycans A1 – A4 = mono- to tetraantennary N-glycans ST6-oe: Clone having sialyltransferase ST6GAL1 overexpressed ST6-oe+GNT3/4: Clone having sialyltransferase ST6GAL1 overexpressed and B4GALNT3 and B4GALNT4 knocked-out.

Ref: WT clone

GNT3-KO: Clone having B4GALNT3 knocked-out

GNT4-KO: Clone having B4GALNT4 knocked-out

GNT3/4-KO: Clone having B4GALNT3 and B4GALNT4 knocked-out

Fig. 2:

| | **harvest** | **GalNAc>0** |
|---|---|---|
| FVII-H9D8 P1004-A2 (WT) | early harvest | 34 |
| | mid harvest | 29 |
| | late harvest | 28 |
| FVII-P1172-H8 pool (GNT 3/4 KO) | early harvest | 0 |
| | mid harvest | 0 |
| | late harvest | 0 |
| FVII-H9D8 P1004-A2 ST6 GalNAc KO P1130-A7 (ST6-oe+GNT3/4 KO) | early harvest | 0 |
| | mid harvest | 0 |
| | late harvest | 0 |

MEANS AND METHODS FOR MODIFYING MULTIPLE ALLELES

CROSS-REFERENCE TO RELATED APPLICATIONS

This application claims priority to International Application No. PCT/EP2017/065010, filed on Jun. 20, 2017, which claims the benefit of foreign Applications Nos. EP 16001385.0 filed on 20 Jun. 2016 and of LU93251 filed on 07 Oct. 2016, the contents of which are incorporated by reference in their entireties. Also, the entire contents of the ASCII text file entitled "IPM0089US_Sequence_Listing.txt" created on Dec. 18, 2018, having a size of 6524 bytes is incorporated herein by reference.

TECHNICAL FIELD OF THE INVENTION

The present invention relates to a method of modifying at least one gene in a cell via CRISPR/Cas, wherein the at least one gene has at least three alleles. The present invention further relates to cells obtainable by the method of the invention. Additionally, the present invention provides a method of producing a protein in a cell obtainable by the method of modifying at least one gene of the invention. Moreover, the invention relates to proteins obtainable by the method of producing a protein and use thereof, for example in therapy.

BACKGROUND ART

The Clustered Regularly Interspaced Short Palindromic Repeats (CRISPR) and CRISPR Associated (Cas) system (CRISPR/Cas system) was first discovered in *E. coli* (Ishino Y et al., J Bacteriol. 1987 December; 169 (12): 5429-33) and has been found later on to represent a bacterial immune system. Its physiological function appears to confer bacteria protection against foreign DNA invading the cell, e.g. in the form of plasmids or viral nucleic acids. Briefly, upon exposition to bacteriophages or plasmids and an accompanying uptake of foreign DNA, bacterial enzymes degrade the foreign DNA into short segments which are incorporated in the bacterial genome in a CRISPR locus. These "foreign sequences" are termed "spacers". In a CRISPR locus, these spacers are separated by short palindromic repeats. The CRISPR locus is transcribed into a pre-CRISPR RNA (pre-crRNA) which is then cleaved into smaller units (crRNAs) each comprising a spacer acting as a targeting sequence for foreign DNA. The targeting sequence is involved in recognition of its complementary sequence on the target DNA to be degraded. However, a further requirement for successful activation of the CRISPR system is the presence of a specific sequence downstream of the target sequence on the DNA to be degraded, namely the protospacer adjacent motif (PAM). A further component of the complex which binds to the target DNA is Cas9 nuclease. In case of sufficient homology between the "spacer derived" RNA and the target DNA, Cas9 separates the double stranded target DNA and introduces a double strand break in vicinity of the PAM. The resulting double strand break can then be repaired by general repair pathways such as the Non-Homologous End Joining (NHEJ) pathway or the Homology Directed Repair (HDR) pathway. The first is rather efficient but error-prone, while the latter one has the opposite properties. Especially NHEJ results in small nucleotide insertions or deletions at the site of the double strand break. Depending on the number of nucleotides which are inserted or deleted, or depending on the type of nucleotides inserted, such repair can result in amino acid insertions, deletions or substitutions in the resulting protein or in introduction of a frame shift, which can result in introduction of pre-mature stop codons and generate truncated proteins. Since the NHEJ repair of the double strand break is random, a population of cells subjected to a CRISPR system will result in an array of mutations at the target site. Since their discovery as bacterial immune system, CRISPR/Cas systems have been in the focus of diverse research activities. In a pioneering work of J. Doudna and E. Charpentier, it has been shown that CRISPR/Cas systems are highly useful tools for genome editing (Jinek et al., Science 17 Aug. 2012: Vol. 337, Issue 6096, pp. 816-821; DOI: 10.1126/science.1225829). Previously, genome editing approaches relied on zinc finger nucleases (ZFNs) or transcription-activator-like effector nucleases (TALENs). A major drawback of these systems was the necessity to specifically design nuclease proteins for genomic targets. In contrast thereto, recognition of genomic targets by the CRISPR/Cas systems is mediated by short RNA sequences, thereby providing a much more accessible system.

Although, CRIPSR/Cas is nowadays widely applied, there is still a need for the development of further applications of CRISPR/Cas, in particular for complex applications in order to facilitate multiple modifications in a cell in a least minimal number of steps.

The technical problem is thus to comply with this need.

The solution to this technical problem underlying the present invention is achieved by providing the embodiments characterized in the claims. The invention is further defined by the embodiments reflected in the claims, described in the description, and illustrated in the Examples and Figures.

SUMMARY OF THE INVENTION

Accordingly, the present invention relates to a method of modifying at least one gene in a cell via CRISPR/Cas, wherein the at least one gene has at least three alleles.

Multiplex genome engineering is for certain approaches desirable. However, if genes encoding proteins having an identical, redundant, or at least overlapping function, it cannot be judged by virtue of the phenotype of the genome-edited cell whether or not the desired genes were edited in a multiplexing approach. Moreover, among two or more of such genes, it cannot be excluded a priori that one or more of them are preferentially targeted by the CRISPR approach which would render such an approach rather cumbersome. Besides, a multiplex approach may not be calculable a priori when targeting one or more genes in cells which have three or more alleles of the targeted genes, e.g. when the cells are polyploid in the target gene loci.

However, despite these various challenges with a multiplex approach that could have been expected as explained before, the present inventors successfully applied a multiplex genome editing approach by applying CRISPR/Cas. Specifically, they were able to modify at least one gene in a cell, wherein the gene has at least three alleles.

More specifically, by way of example, which example is a preferred embodiment of the present invention, the present inventors were successful in targeting multiple loci of two genes having multiple alleles. This is exemplified for B4GALNT3 and B4GALNT4. B4GALNT3 was determined to have 3 alleles and B4GALNT4 was determined to have 4 alleles. In order to modify both genes, the present inventors targeted 2 exons in each allele of B4GALNT3 and 2 exons in each allele of B4GALNT4. This sums up to 14 loci which were targeted in parallel. Given the redundant function of B4GALNT3 and B4GALNT4 and the various alleles, it could not have been expected that a multiplex genome editing approach by using CRISPR/Cas would be successful.

The following example is provided for illustrating, but not limiting the present invention. With the aim of optimizing glycosylation with regard to the reduction of liver receptor binding properties, the present inventors chose to eliminate the capability of host cells to incorporate N-acetylgalactosamine (GalNac) residues into glycan structures that are attached to proteins, typically via so-called N-glycosylation. GalNac moieties exhibit high affinity towards the asialoglycoprotein receptor in the liver which binds proteins having GalNac residues and internalizes them, thereby eliminating such proteins from the circulation. This has an impact on therapeutic proteins which are oftentimes desired to remain in the circulation for a prolonged time in order to exert their therapeutic potential. Accordingly, the present inventors chose to eliminate activity conferred by the proteins encoded by the B4GALNT3 and B4GALNT4 genes. These genes encode proteins having beta-1,4-N-acetyl-galactosaminyltransferase 3 activity (GalNT3) and beta-1,4-N-acetyl-galactosaminyltransferase 4 (GalNT4), respectively. Much to their surprise, the present inventors observed—in addition to have been able to target multiple alleles of at least one gene by way of a genome-editing approach—that the elimination of the activity of the two GalNT genes led to unexpected changes in other N-glycan features like antennarity of the N-glycans as well as the sialylation degree.

In particular, the present inventors in order to eliminate GalNAc residues the two respective transferases (GalNT) were knocked out with the CRISPR/Cas9 technology singly as well as simultaneously. To reduce the risk of off-target effects the Cas9 nickase can be used which introduces single strand breaks (SSB) and requires two guideRNAs (gRNA). Each GALNT gene was targeted in two loci simultaneously, whereby the distance between the targets was different.

The genome-editing in the two GalNTs can be detected with a T7 Endonuclease I Assay and positive clones can be rescreened with a Cas9 in vitro assay which allows identification of monoallelic and biallelic indels. Due to polyploidy of the host cells the CRISPR treatment, if necessary, can be repeated on potential knockout clones.

Deep Amplicon Sequencing of candidate clones on the respective loci of B4GALNT3 and B4GALNT4 revealed that more than 80% single knockout clones were mutated in all alleles and that all double knockout clones contained no wt allele.

To this end, by the simultaneous knockout of both genes (B4GALNT3 and B4GALNT4) the GalNAc residues were removed completely and more tetra-antennary structures were present but without full sialylation, thereby achieving a prolonged half-life of a glycosylated protein. However, if desired, a sialyltransferase, preferably a human sialyltransferase, more preferably human ST6GAL1 (ST) as is known and also described herein may be (over)expressed in the double knock out clones in order to achieve full sialylation which will also contribute to a prolonged half-life of a glycosylated protein.

Further, it was shown that after N-acetylgalactosamine (GalNac) knock-out (KO), GalNac was not being expressed anymore even over a longer cultivation time (early to late harvest), which demonstrates that the GalNac KO clones are stable (FIG. 2). In this context, the term "stable" refers to 3-9 days (also 4, 5, 6, 7, 8 days), which refer to early harvest, or 10-16 days (also 11, 12, 13, 14, 15 days), which refer to mid harvest or 17-23 days (also 18, 19, 20, 21, 22 days), which refer to late harvest.

Overexpresison may be achieved by using a strong constitutive or inducible promoter. Overexpression may also be achieved by integrating multiple copies of sialyltransferase into the genome of a host cell, whereby expression of sialyltransferase is driven by a strong constitutive or inducible promoter.

The invention further relates to a cell obtainable by the method of modifying at least one gene in a cell of the present invention.

Additionally, the present invention relates to a method of producing a protein in a host cell, comprising the steps of:

a) introducing at least one nucleic acid encoding said protein in a cell obtainable by the method of modifying at least one gene in a cell;
b) culturing said host cell under conditions which permit the production of said protein; thereby producing the protein.

The invention also relates to a protein obtainable by the method of producing a protein in a host cell, as well as to said protein for use as a medicament.

The present invention is in the field of genome editing and aims at introducing modifications at specific positions of the genome of a cell in order to provide a cell having a different genotype than the cell on which the method is practiced.

BRIEF DESCRIPTION OF THE FIGURES

FIG. 1: Results of N-glycan profiling for clones ST6-oe, ST6-oe+GNT3/4, Ref, GNT3-KO, GNT4-KO and GNT3/4-KO, given in mol % of total glycans.

FIG. 2: N-Glycan bound GalNAc throughout production of all three cell lines (FVII-H9D8 P1004-A2, FVII-H8 pool and FVII-H9D8 P1004-A2 ST6 GalNAc KO P1130-A7) at early harvest, mid harvest and late harvest, given in mol % of total glycans.

DETAILED DESCRIPTION OF THE INVENTION

Thus, in a first aspect, the present invention relates to a method of modifying at least one gene in a cell via CRISPR/Cas, wherein the at least one gene has at least three alleles.

As used herein, the term "modifying a gene" refers to introducing changes in the nucleotide sequence of a coding and/or regulatory region of the gene.

As used herein, the term "allele" refers to one of a number of alternative forms of a gene or genetic locus. Alleles can have the same nucleotide sequence or they can have different amino acid sequences varying in one or more nucleotides over the length of the gene or genetic locus.

As used herein, the term "gene having at least three alleles" refers to a situation that, within a single cell, at least three alleles of the gene are present, i.e., there are at least three distinct nucleic acid stretches in the genome of the cell which encode the gene. Again, the alleles or nucleic acid stretches can have the same nucleotide sequence or they can have different amino acid sequences as recited above in the context of the definition of the term "allele". In other words, the term "gene having at least three alleles" signifies that, in the genome of the cell, there are at least three "copies" of the gene, which, however, do not necessarily have an identical nucleotide sequence. This applies analogously to situations wherein a gene has at least four, five, six, etc. alleles.

In a preferred embodiment, the present invention relates to a method of modifying at least two genes in a cell via CRISPR/Cas, wherein at least one of the two genes has at least three alleles.

In an even more preferred embodiment, the present invention relates to a method of modifying at least two genes in a cell via CRISPR/Cas, wherein a first gene has at least three alleles and a second gene has at least three alleles, preferably the second gene has four alleles.

In general, when modifying at least one gene, it is possible that at least one, two, three, four, five, six or all alleles of the at least one gene are modified. In case of modifying at least two genes, it is possible that at least one, two, three, four, five, six or all alleles of the at least two genes are modified. When several alleles of a gene are modified, it is not necessary that the modification results in identical nucleotide sequences of the alleles. For an allele to be classified as modified, it is sufficient that its nucleotide sequence differs from the original nucleotide sequence, i.e. from the nucleotide sequence before the allele was modified.

In a preferred embodiment, the at least one gene or the at least two genes is/are targeted in at least one, preferably in two, position(s) of the nucleotide sequence of its/their coding and/or regulatory region(s). It is also possible to target the at least one gene or the at least two genes in more than two positions, e.g. in three, four, five, six or more positions.

As used herein, the term "targeting a gene in at least one position" refers to designing a CRISPR/Cas systems to be, in theory, capable of modifying the gene in at least one position. In consequence, "targeting a gene in two positions" refers to designing a CRISPR/Cas systems to be, in theory, capable of modifying the gene in two positions. In this context, a "position within a gene" or "locus" refers to a specific portion of the nucleotide sequence of a coding and/or regulatory region of the gene. In general, in order to introduce a pre-mature stop codon or to generate a modified gene encoding a variant of the encoded protein, it is advantageous to target positions which are located in exons of the gene. For instance, a first position can be on a first exon of the gene and a second position can be on a second exon of the gene.

In certain cases, it is advantageous to target a gene in more than one position, e.g. in two or more positions. Especially when seeking to modify more than one allele of a gene, it is conceivable that not all alleles are successfully modified in the resulting cell. For example, it is possible that only one allele is modified and at least one other allele is not modified. Thus, by targeting the gene in two or more positions, the likelihood that each allele is successfully modified in at least one position is increased.

In a preferred embodiment, the cell is polyploid in at least one gene, preferably in at least one of the genes to be modified. In a more preferred embodiment, the cell is diploid, triploid or tetraploid in at least one of the genes. In an even more preferred embodiment, the cell is triploid in a first gene and tetraploid in a second gene. In this context, it is especially preferred that the first gene and/or the second gene are to be modified, while it is most preferred that both the first gene and the second gene are to be modified.

In general, the term "polyploid cell" is known to a skilled person and denotes the phenomenon that a cell contains more than two sets of chromosomes. In most animals, and also in humans, somatic cells are diploid, i.e. they contain two sets of chromosomes. In contrast thereto, human gametes are haploid, i.e. they contain only one set of chromosomes. The term "polyploid" comprises the terms "triploid" (i.e. containing three sets of chromosomes), "tetraploid" (containing four sets of chromosomes), "pentaploid" (containing five sets of chromosomes) and so on.

It is also possible that a cell is "polyploid in a gene", i.e. the genome of the cell contains more than two (such as three, four, five or more) nucleic acid stretches encoding the gene, while the cell can be, for example, haploid or diploid in other genes, i.e. the genome of the cell contains one (haploid) or two (diploid) nucleic acid stretches encoding the other genes.

In a preferred embodiment of the present invention, the fact that a gene has multiple, e.g. three, alleles results from the fact that the cell is polyploid, e.g. triploid, in this gene.

In a preferred embodiment of the present invention, modifying at least one gene via CRISPR/Cas results in introduction of one or more insertion(s), deletion(s) and/or substitution(s) of one or more nucleotides or a combination thereof in a coding and/or regulatory region of the at least one gene.

As stated above, modifying a gene generally refers to introducing changes in the nucleotide sequence of a coding and/or regulatory region of the gene. According to the present invention, the modifications are induced via CRISPR/Cas. The general steps and features of the CRISPR/Cas procedure are known to a skilled person. Specific details of the method of the present invention will be detailed later on. However, it can already be stated that modifying a nucleic acid such as genomic DNA via CRISPR/Cas results in a double strand break of the DNA in close vicinity to the nucleotide sequence complementary to the target sequence of the crRNA. Double strand repair usually proceeds via endogenous cellular DNA repair mechanisms such as NHEJ. These mechanisms result in random addition and/or deletion of nucleotides, thereby producing a "repaired" nucleic acid which may differ in length from the original nucleic acid by one or more nucleotides. For example, the "repaired" nucleic acids may be at least 1, 2, 3, 4, 5, 6, 7, 8, 9, 10, 12, 14, 16, 18, 20, 25, 30, 35, 40, 45, 50, 55, 60, 65, 70 or more nucleotides longer or shorter than the original sequence. Thus, the changes introduced in the nucleotide sequence of a coding and/or regulatory region of the gene can be selected from one or more insertion(s), deletion(s) and/or substitution(s) of one or more nucleotides or a combination thereof. Such changes, however, can have various effects on transcription and/or translation of the genes.

In a preferred embodiment of the present invention, modifying at least one gene via CRISPR/Cas results in decreased transcription and/or expression of the least one gene and/or in production of a variant of the at least one gene which is truncated and/or has altered enzymatic activity.

In case of a change in the nucleotide sequence of a regulatory region of the gene, transcription of the gene may be affected, e.g. be enhanced or decreased. This may result in increased or decreased protein levels of the gene product in the cell.

In case of a change in the nucleotide sequence of a coding region of the gene, various effects on the encoded protein are conceivable.

For example, modifications of the nucleotide sequence by insertions, deletions or substitutions may result directly in generation of a premature stop codon. Equally, modifications resulting in a frame shift may result indirectly in generation of a premature stop codon. As a consequence thereof, translation of the mRNA will stop prematurely, resulting in generation of a truncated variant of the protein. In case the amino acid stretches which are not present in the truncated variant play a role in structure and/or function of the protein, the protein may have altered biological activity compared to the original protein, or it may have no biological activity at all. In case such modifications do not result in generation of a premature stop codon, it is conceivable that a variant protein having one or more amino acid substitutions results therefrom. Since the amino acid sequence of a protein is its primary structural determinant, these modifications can have an effect on overall protein structure and thereby on protein function. Depending on the extent of sequence variation between the modified variant gene and the original gene, there may be minor or major effects on protein function, which can have either positive or negative effects on protein function, i.e. result in increased or decreased protein activity.

In general, the coding region of a gene can comprise one or more nucleotide sequence portions which encode one or more domains of a protein. Distinct domains of a protein may have different functions, e.g. substrate binding, enzymatic activity, protein targeting. Thus, a localization of a modification within a specific domain may restrict the effects caused by the modification to specific biological activities mediated by said domain. By specifically targeting a specific domain in the method of the present invention, it may be possible to specifically target biological activities mediated by said domain.

Modifying a gene in a cell via CRISPR/Cas according to the present invention comprises providing knockout or knockdown mutants of a gene or generating protein variants with altered activity. As used herein, a "knockout" relates to a situation wherein no functional protein is produced from the modified gene. As used herein, a "knockdown" relates to a situation wherein a decreased amount of functional protein is produced from the modified gene and/or wherein the protein has decreased activity compared to the original protein. A protein variant with altered activity may have either increased or decreased activity compared to the original protein, or it may have altered properties such as altered substrate specificity.

It may also be possible to deliberately modify the nucleotide sequence after introducing a double strand break, e.g. by relying on HDR for double strand break repair and providing homologous DNA molecules including the purposefully modified sequence. Thus, the presented method can also be adapted for targeted gene editing In a preferred embodiment of the present invention, the cell is a human cell or is derived from a human cell. The cell can be of any cell type found in the human body. Preferably, the cell is a blood cell, kidney cell, lung cell or a fibroblast. In a more preferred embodiment, the cell is an immortalized cell, for example an immortalized human blood cell. In a specific embodiment, the cell is of human myeloid leukaemia origin or is derived therefrom. Exemplary cells include H9D8 having the DSMZ accession number DSM ACC 2806, NM-H9D8-E6Q12 [DSM ACC2856]; GT-5s [DSM ACC 3078]. It is also possible to use cells derived from the above cells or subclones thereof.

The term "subclones", when used in accordance with the present invention, means cells which are derived from a cell or cell line (e.g. from H9D8 cells) and which occur due to naturally occurring alterations, e.g., mutations, but have similar characteristics as the original cells or cell lines.

According to the present invention the term "cell" or "cell line" means a cell line or cells which can be grown under in vitro culture conditions as indicated, e. g., in the appended examples. Additionally, said term also embraces cells of a single type that have been grown in the laboratory for several generations. The term "H9D8", as used herein, relates to cells of a cell line or a cell line deposited with the Deutsche Sammlung für Mikroorganismen and Zellkulturen GmbH ("DSMZ") having the deposit number DSM ACC 2806 and is described in detail in WO 2008/028686 A1.

In accordance with the present invention the term "cell of human myeloid leukemia origin" or equivalent formulations means any cell or cell line of human myeloid leukemia origin, or any human myeloid or myeloid precursor cell or cell line which can be obtained from a leukemia patient, or any myeloid or myeloid precursor cell or cell line which can be obtained from a human donor, or a cell or cell line derived from anyone of said host cells, or a mixture of cells or cell lines comprising at least one of those aforementioned cells.

In another embodiment of the invention said cell of human myeloid leukemia origin or said immortalized human blood cell also comprise such cells or cell lines which were obtained by fusing at least one of the aforementioned cells, in particular those of myeloid leukemia origin, with another cell of human or animal origin, such as but not limited to B cells, CHO cells. Those skilled in the art are able to identify and use suitable sources and methods to obtain, generate and/or immortalize suitable cells and cell lines from humans for suitable cells of human myeloid leukemia origin.

Independently of verifying successful modification of at least one gene having at least three alleles, cells which have been modified in a gene can be further selected due to general properties of those cells which are advantageous when compared to their parent cell or cell line such as but not limited to shorter doubling times, faster growth, possibility to grow under higher densities, are growing under serum free conditions and/or in protein free media, higher cloning efficiencies, higher transfection efficiencies for DNA, higher expression rates of protein molecule compositions, higher activities for a protein molecule composition expressed therein, higher homogeneities of a protein molecule composition expressed therein, and/or higher robustness to scaling up. Methods for selecting those cells with advantageous properties are known to those skilled in the art. In a preferred embodiment, in which the cell to be modified is intended for producing glycoproteins, said cell or cell line derived from said cells can be further selected by binding to a lectin or carbohydrate-binding antibody. It is also possible to perform such general selection steps before genetically modifying the cells.

In the method of modifying at least one gene having at least three alleles in a cell, CRISPR/Cas is used. The general procedure of this technique is known to a skilled person. As used herein, the term "CRISPR/Cas system" refers to all components, in particular to all nucleic acid and protein components, necessary for modifying at least one gene via CRISPR/Cas. Thus, this term also comprises a plurality of independent guide RNA (gRNA) molecules targeting the same or different positions within a gene. gRNAs are also denoted as single guide RNAs (sgRNAs). Corresponding protocols for CRISPR/Cas are readily available. For example, suitable target sites on the nucleic acid to be targeted can be chosen using the DNA2.0 CRISPR gRNA Design tool (https://www.dna20.com/eCommerce/cas9/input). For example, sgRNA plasmids can be constructed according to a protocol of Prashant Mali (Church Lab), Version: 01-14-2013 (https://www.addgene.org/static/cms/files/hCRISPR gRNA Synthesis.pdf), preferably according to Option A. A suitable Cas protein is CRISPR Cas9-D10A Nickase Plasmid (Sigma, #CAS9D10AP-1EA). A detailed way of carrying out the invention according to the present claims is given in the accompanying examples.

In a preferred embodiment of the present invention, for each position to be targeted the CRISPR/Cas system comprises two gRNA plasmids, each gRNA plasmid comprising a specific targeting sequence. However, it may also be preferred that the specific targeting sequences are on one gRNA plasmid. Accordingly, when relying on a CRISPR/Cas system for generating a genetically modified host cell according to the present invention, it may be preferred that for each position to be targeted the CRISPR/Cas system comprises one gRNA plasmid containing the specific targeting sequences.

It may also be preferred that also the nucleotide sequence encoding the Cas enzyme is contained on the gRNA plasmid. However, in the alternative, the nucleotide sequence encoding the Cas enzyme may also be contained on an extra plasmid, i.e., not contained on the gRNA plasmid.

According to the present invention, a method of modifying at least one gene in a cell via CRISPR/Cas, wherein the at least one gene has at least three alleles, comprises the following steps:

a) selecting a cell;

b) selecting at least one gene, preferably selecting at least two genes, in the cell;

c) determining the number of alleles present for the at least one gene in the cell, preferably for the at least two genes, unless this allele frequency is already known;

d) choosing suitable target sites for each gene to be modified, optionally for each position within a gene to be modified;

e) constructing sgRNA plasmids;

f) transfecting the cells with one or more plasmids encoding a Cas protein and the gRNA molecules;

g) cultivating the cells.

The method can further comprise the following steps:

h) isolating and expanding single clones;

i) verifying modification of the at least one gene having at least three alleles, preferably of the at least two genes having at least three alleles, in single clones, e.g. by genotypic analysis of single clones.

Optionally, steps d) to g), preferably steps f) to g), can be repeated, either directly following step g) or following step h) or step i).

For example, in step c), the number of alleles present for a specific gene in the cell (allele frequency) can be determined on the basis of whole genome sequencing (WGS) data.

For example, in step f), transfection of cells with plasmids can be conducted by nucleofection. For example, in step h), isolation and expansion of single clones can be achieved by a ClonePix FL system.

For example, in step i), verifying modifications of a gene can be conducted by various methods such as analysis of PCR fragment length, T7 Endonuclease-I (T7EI) assay, in vitro Cas9 assay, and/or sequencing methods such as Deep Amplicon Sequencing.

The T7EI assay can be used to get a first estimate of genome targeting efficiency. T7 Endonuclease I recognizes and cleaves non-perfectly matched DNA. Upon successful introduction of a gRNA/Cas9 mediated cut and subsequent non-perfect repair, modified DNA strands are generated. When these modified strands anneal with DNA strands without modification, a substrate for T7EI is generated. In a first step, genomic sequences of interest are amplified by PCR. In a second step, PCR products are annealed and digested with T7 Endonuclease I, thereby generating smaller fragments when heteroduplexes are present.

The in vitro Cas9-Assay is based on the recombinant Cas9 endonuclease that is guided to its target by sequence complementarity of a small gRNA loaded into the protein. This assay is used after modifying genes to determine whether a given clone has solely mutated alleles, a mix of mutated and wildtype alleles or has solely unchanged alleles (wild type) (wild type). The protocol involves amplification of the target site and in vitro cleavage with Cas9 and the gRNA used for the original CRISPR/Cas9 gene modification experiment. If indels (insertions or deletions) are present at the target site, the original gRNA/Cas9 complex will be unable to cleave the site, whereas wild-type alleles will be recognized and cleaved. In this assay, smaller fragments are indicative of the presence of wild type alleles.

The recited exemplary methods are not to be construed to limit the scope of the invention. Specific examples are given in the Examples section accompanying the description.

In a specific embodiment of the present invention, the at least one gene is B4GALNT3, B4GALNT4 or glutamine synthetase, preferably GLUL glutamate-ammonia ligase ENSG00000135821; NCBI Gene ID: 2752. Preferably, the at least two genes are B4GALNT3 and B4GALNT4. More preferably, the first gene is B4GALNT3 and the second gene is B4GALNT4.

In a very specific embodiment of the present invention, the cell is a H9D8 cell or a cell derived therefrom, and the first gene is B4GALNT3 and the second gene is B4GALNT4. In H9D8, B4GALNT3 has three alleles, and B4GALNT4 has four alleles.

B4GALNT3 (NCBI Gene ID: 283358; updated on 5 Jun. 2016 encodes Beta-1,4-N-Acetyl-Galactosaminyl Transferase 3. B4GALNT3 transfers N-acetylgalactosamine (GalNAc) onto glucosyl residues to form N,N-prime-diacetyllactosediamine (LacdiNAc, or LDN), a unique terminal structure of cell surface N-glycans (Ikehara et al., 2006 [PubMed 16728562]). B4GALNT3 is located on human chromosome 12 (Start: 460,364 bp from pter; End: 563,509 bp from pter; Size: 103,146 bases; Orientation: Plus strand; Cytogenetic band: 12p13.33 by Ensembl; 12p13.33 by EntrezGene). Currently, two polypeptides produced from B4GALNT3 are known. Variant 1: Size: 998 amino acids, Molecular mass: 114975 Da; Variant 2: Size: 636 amino acids, Molecular mass: 73000 Da. Variant 2 is a splice variant. B4GALNT3 is glycosylated at Ser70 (cf. http://www.nextprot.org; ID: NX_Q6L9W6). Known subcellular localizations of B4GALNT3 are Golgi apparatus (Golgi stack membrane); Single-pass type II membrane protein.

An important paralog of this gene is B4GALNT4 (NCBI Gene ID: 338707; updated on 5 Jun. 2016) which encodes Beta-1,4-N-Acetyl-Galactosaminyl Transferase 4. B4GALNT4 transfers N-acetylgalactosamine (GalNAc) from UDP-GalNAc to N-acetylglucosamine-beta-benzyl with a beta-1,4-linkage to form N,N-diacetyllactosediamine, GalNAc-beta-1,4-GlcNAc structures in N-linked glycans and probably O-linked glycans. B4GALNT4 is located on human chromosome 11 (Start: 369,779 bp from pter; End: 382,117 bp from pter; Size: 12,339 bases; Orientation: Plus strand; Cytogenetic band: 11p15.5 by Ensembl; 11p15.5 by EntrezGene). B4GALNT4 comprises 1039 amino acids and has a molecular mass of 116513 Da. B4GALNT4 is glycosylated at Asn105 (cf. http://www.nextprot.org; ID: NX_Q76KP1). Known subcellular localizations of B4GALNT3 are Golgi apparatus (Golgi stack membrane); Single-pass type II membrane protein.

In an especially preferred embodiment B4GALNT3 and B4GALNT4 are each targeted in two positions. For example, each gene can be targeted in two different exons. For a specific example, reference is made to the accompanying Examples section.

When modifying B4GALNT3 and/or B4GALNT4, in a preferred embodiment of the present invention, combinations of the following targeting sequences can be used: the targeting sequences specific for B4GALNT3 are selected from ATTGCTGCAGATGACAACG (SEQ ID NO: 1)/TGGATTTTCCCTGGGCAGC (SEQ ID NO: 2) and CCCGGGACACCCTCTATCG (SEQ ID NO: 3)/GGCCGAAGCATGTCAGCGGG (SEQ ID NO: 4); and/or the targeting sequences specific for B4GALNT4 are selected from GCGTGCACTTGTGTATTCG (SEQ ID NO: 5)/CCACAGTCACTCACCGCCT (SEQ ID NO: 6) and GGTTTCATCCACCCGGCGA (SEQ ID NO: 7)/GAGTCCATAGTTCTTCCACT (SEQ ID NO: 8).

In general, other genome editing techniques, e.g. relying on artificially engineered nucleases such as zinc finger nucleases (ZFNs), meganucleases or transcription-activator-like effector nucleases (TALENs) or a CRISPR/Cas system can also be used for modifying at least one gene according to the present invention, e.g. B4GALNT3 and B4GALNT4.

In a second aspect, the present invention relates to a cell obtainable by a method of modifying at least one gene in a cell via CRISPR/Cas, wherein the at least one gene has at least three alleles. Regarding this second aspect, all statements made with regard to the first aspect are applicable.

A "cell" when referred to herein in the context of methods and cells includes a host cell.

The cell of the second aspect of the invention can be useful in a variety of applications. For example, the cell can be useful for producing human glycoproteins, especially when B4GALNT3 and/or B4GALNT4 are modified. Accordingly, the present invention provides a cell having one or more genetic modification(s) within a coding and/or regulatory region of B4GALNT3 and/or B4GALNT4. Such a cell may, for example, be obtainable by genome-editing, preferably by applying CRISPR/Cas as described herein with regard to methods of modifying at least one gene in a cell via CRISPR/Cas.

Modifications may by insertions, deletions or substitutions that result in the reduction, preferably elimination of the activity of the protein encoded by B4GALNT3 and B4GALNT4, respectively. B4GALNT3 and B4GALNT4 encode proteins having beta-1,4-N-acetyl-galactosaminyltransferase 3 activity (GalNT3) and beta-1,4-N-acetyl-galactosaminyltransferase 4 (GalNT4), respectively.

Such cells, when used for the production of a protein of interest surprisingly showed, apart from the absence of GalNac residues within N-glycans, increased tetra-antennary structures within N-glycans and/or increased sialylation and/or decreased outer arm fucosylation (antennary fucosylation) in comparison to cells which do not have one or more genetic modifications within a coding and/or regulatory region of B4GALNT3 and/or B4GALNT4. It could not have been expected that a modification of B4GALNT3 and/or B4GALNT4 would have led to the absence of GalNac residues within N-gylcans, since cells also have further N-acetyl-galactosaminyltransferases which could have taken over the function of B4GALNT3 and/or B4GALNT4.

All the more, it could not have been expected that a modification of B4GALNT3 and/or B4GALNT4 would have an influence on tetra-antennary structures and/or increased sialylation and/or outer arm fucosylation. Indeed, absence of GalNac within N-glycans and increased sialylation prolongs the half-life of a glycosylated protein produced by such a cell and the reduction of outer arm fucose renders a glycosylated protein less immunogenic.

Thus, in a third aspect, the present invention relates to a method of producing a protein in a host cell, comprising the steps of:

a) introducing at least one nucleic acid encoding said protein in a cell as described in the context of the second aspect of the present invention;
b) culturing said host cell under conditions which permit the production of said protein; thereby producing the protein.

Additionally or alternatively to said step a), the nucleic acid may already be present in said cell and/or may already have been introduced in the cell before being genetically modified according to the first aspect of the invention, thereby anticipating said step a).

The protein which is produced in step b) can be further purified or isolated by any suitable method known in the art.

In general, there is no limitation to the origin, size or structure of the protein to be produced. Thus, the method according to the third aspect of the invention can be useful for various applications.

In a preferred embodiment of the present invention, the protein is a naturally occurring protein, an artificially created protein or a fragment thereof. It is especially preferred that the protein is glycosylated, i.e. that it is a glycoprotein. In an especially preferred embodiment of the present invention, the protein is a human protein, preferably a human glycoprotein. When genes involved in glycosylation are modified according to the first aspect of the present invention, it may be possible to produce specific glycoforms of a protein from the resulting host cell. The term "glycoform" of a protein refers to an isoform of a protein differing with respect to the number or type of attached glycans. Thus, a specific glycoform will have a specific glycosylation pattern which may be influenced by the glycosylation machinery of the host coll. For example, carbohydrate chains of different glycoforms may differ in their composition and/or organisation. For example, additional building blocks such as galactose, sialic acid, bisecGlcNAc, fucose, or other carbohydrate units may be present, or acetylation or sulfatation may be different for different glycoforms. Alternatively, such building blocks may be lacking from a specific glycoform. In this regard, it will be especially useful to choose the above mentioned genes B4GALNT3 and/or B4GALNT4 as the genes to be modified. These genes are part of the glycosylation machinery of mammalian cells. Thus, cells which are genetically modified in these genes may be useful in producing specific glycoforms of a protein molecule.

In addition to proteins or glycoproteins, also other molecules may be obtained from the cells according to the second aspect of the invention. In this context, such molecules can be for example glycolipids. It is also possible to produce more than one type of molecule in a host cell at the same time. For example, it is also possible to produce two different proteins at the same time.

According to this aspect of the present invention the term "protein" or "protein molecule" is encompassed by the term "protein of interest". It encompasses thus any protein of interest or active fragments and/or mutants thereof whereby any protein can be used, preferably any glycoprotein of human origin. The term protein molecule means any polypeptide molecule or a part thereof. It can be encoded by one or several nucleic acids. It can be produced in a secretory fashion or a fraction thereof or a fusion protein with a fusion partner. Preferably, the protein is secreted into the supernatant. This embodiment is in particular beneficial regarding the overall production process, as e.g. shedding steps (e.g. with phorbol esters) can be avoided.

Examples of mammalian glycoproteins include molecules such as cytokines and their receptors, for instance the tumor necrosis factors TNF-alpha and TNF-beta; renin; human growth hormone and bovine growth hormone; growth hormone releasing factor; parathyroid hormone; thyroid stimulating hormone; lipoproteins; alpha-1-antitrypsin; insulin A-chain and B-chain; gonadotropins, e.g. follicle stimulating hormone (FSH), luteinizing hormone (LH), thyrotrophin, and human chorionic gonadotrophin (hCG); calcitonin; glucagon; clotting factors such as factor VIIIC, factor IX, factor VII, tissue factor and von Willebrand factor; anti-clotting factors such as protein C; atrial natriuretic factor; lung surfactant; plasminogen activators, such as urokinase, human urine and tissue-type plasminogen activator; bombesin; thrombin; hemopoietic growth factor; enkephalinase; human macrophage inflammatory protein; a serum albumin such as human serum albumin; mullerian-inhibiting substance; relaxin A-chain and B-chain; prorelaxin; mouse gonadotropin-associated peptide; vascular endothelial growth factor; receptors for hormones or growth factors; integrin; protein A and D; rheumatoid factors; neurotrophic factors such as bone-derived neurotrophic factor, neurotrophin-3, -4, -5, -6 and nerve growth factor-beta; platelet-derived growth factor; fibroblast growth factors; epidermal growth factor; transforming growth factor such as TGF-alpha and TGF-beta; insulin-like growth factor-I and -II; insulin-like growth factor binding proteins; CD proteins such as CD-3, CD-4, CD-8 and CD-19; erythropoietin (EPO); osteoinductive factors; immunotoxins; a bone morphogenetic protein; an interferon such as interferon-alpha, -beta, and -gamma; colony stimulating factors (CSFs), e.g. M-CSF, GM-CSF and G-CSF; interleukins (ILs), e.g. IL-1 to IL-12; superoxide dismutase; T-cell receptors; surface membrane proteins; decay accelerating factor; antibodies and immunoadhesins; Glycophorin A; MUC1.

Many of the aforementioned glycoproteins belong to the cytokines, herein referring to the general class of hormones occurring in cells of the immune system, both lymphokines and monokines, and others. The definition is meant to include, but is not limited to, those hormones that act locally and do not circulate in the blood, and which, when used in accordance with the present invention, will result in an alteration of an individual's immune response. Examples of further suitable immunomodulatory cytokines include, but is not limited to, interferons (e.g. IFN-alpha, IFN-beta and IFN-gamma), interleukins (e.g. IL-1 , IL-2, IL-3, IL-4, IL-5, IL-6, IL-7, IL-8, IL-9, IL-10 and IL-12), tumor necrosis factors (e.g. TNF-alpha and TNF-beta), erythropoietin (EPO), FLT-3 ligand, macrophage colony stimulating factor (M-CSF), granulocyte colony stimulating factor (G-CSF), granulocyte-macrophage colony stimulating factor (GM-CSF), CD2 and ICAM. Taking erythropoietin, the molecule is believed to cause progenitor cells to mature into erythrocytes whereas thrombopoietin is thought to drive progenitor cells along the thrombocyte pathway. CSF refers to a family of lymphoicines which induce progenitor cells found in the bone marrow to differentiate into specific types of mature blood cells. The particular type of mature blood cell that results from a progenitor cell depends upon the type of CSF present. Similarly, granulocyte- macrophage colony formation is dependent on the presence of GM-CSF. Additionally, cytokines of other mammals with substantial homology to the human forms of IL-2, GM-CSF, TNF-alpha and others, will be useful in the invention when demonstrated to exhibit similar activity on the immune system. Adhesion or accessory molecules or combinations thereof may be employed alone or in combination with the cytokines.

Similarly, proteins that are substantially analogous to any particular protein, but have relatively minor changes of protein sequence, will also find use in the present invention. It is well known that some small alterations in the amino acid sequence in protein sequence may often be possible without disturbing the functional abilities of the protein molecule, and thus proteins can be made that function as the parental protein in the present invention but differ slightly from current known sequences. Respective variants maintaining the biological function are thus also comprised. Preferred glycoproteins are selected from the group comprising FVII, Glycophorin A, EPO1 G-CSF, GM- CSF, FSH, hCG, LH, interferons, interleukins, antibodies and/or fragments thereof.

Importantly, the present invention is not limited to production of FVII as explained herein. Production of this protein is rather shown as an example. In fact, the advantageous glycosylation characteristics of FVII discussed herein apply to any other glycoprotein, preferably glycoproteins which have N-glycosylation (i.e. N-glycan proteins), since the glycosylation characteristic of a cell is encoded by the cell's genome and is regulated by cellular factors and by this is independent of the gene introduced to the cell.

All protein molecules mentioned above can be fused to other peptide or polypeptide sequences such as but not limited to linker, activating molecules or toxins.

The at least one nucleic acid to be introduced into the cell in step a) may comprise a heterologous sequence. The nucleic acid may be in the form of a vector. Suitable vectors are, e.g., a plasmid, cosmid, virus, phagemide, bacteriophage or any other vector conventionally used in genetic engineering and/or in transfection of mammalian cells. Said vector may be selected from commercially available vectors. Nonlimiting examples include plasmid vectors and expression systems compatible with mammalian cells, such as pcDNA vectors, pSec vectors, pCMV vectors, pCEP4 (all Invitrogen), pRK5, pMC1 neo (Stratagene), pSG5 (Stratagene), pBK vectors (Stratagene) EBO-pSV2neo, pBPV-1, pdBPVMMTneo, pRSVgpt, pRSVneo, pSV2-dhfr, pTRE vectors (Clontech), pet-On/Off vectors (Clontech), and bicistronic and bi-directional vectors (e. g. pIRES vectors, pBI Vectors, Clontech)). For vector modification techniques, see Sambrook and Russel "Molecular Cloning, A Laboratory Manual", Cold Spring Harbor Laboratory, N. Y. (2001). Vectors can contain one or more replication and inheritance systems for cloning or expression, one or more marker genes for selection in the host, e.g., antibiotic resistance, and one or more expression cassettes.

The nucleic acid molecule may be any type of nucleic acid, e. g. DNA or RNA. The DNA may, for example, be genomic DNA, synthetic DNA or cDNA. The RNA may be, e.g., mRNA. The nucleic acid molecule may be natural, synthetic or semisynthetic or it may be a derivative, such as phosphorothioates. Furthermore, the nucleic acid molecule may be a recombinantly produced chimeric nucleic acid molecule comprising any of the aforementioned nucleic acid molecules either alone or in combination. The nucleic acid molecules comprised by said vector can be synthesized by standard methods, isolated from natural sources, or prepared as hybrids. Ligation of the coding sequences to transcriptional regulatory elements (e.g., promoters, enhancers, insulators or the like) and/or to other amino acid encoding sequences can be carried out using established methods. Said vector and/or said nucleic acid can be introduced into cells by methods commonly known in the art, for example, lipofection, electroporation, Ca-phosphate-transfection and the like.

Furthermore, the vectors may comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript.

Additional regulatory elements may include transcriptional as well as translational enhancers, and/or naturally-associated or heterologous promoter regions. Possible regulatory elements permitting expression comprise for example the CMV-HSV thymidine kinase promoter, SV40, RSV-promoter (Rous sarcoma virus), human elongation factor 1a-promoter, CMV enhancer, CaM-kinase promoter or SV40-enhancer. For the expression in cells, several regulatory sequences are well known in the art. For the expression in prokaryotic cells, a multitude of promoters including, for example, the tac-lac-promoter, the lacUV5 or the trp promoter, has been described. Beside elements which are responsible for the initiation of transcription, such regulatory elements may also comprise transcription termination signals, such as SV40-poly-A site or the tk-poly-A site, downstream of the coding sequence. In this context, suitable expression vectors are known in the art such as Okayama-Berg cDNA expression vector pcDV1 (Pharmacia), pRc/CMV, pcDNA1, pcDNA3, pcDNA5 (Invitrogen). An expression vector useful in the invention is at least capable of directing the replication, and preferably the expression, of nucleic acids contained therein. Suitable origins of replication are known to the skilled person and include, for example, the SV40 origin of replication. Suitable termination sequences are known to the skilled person and include, for example, the bovine growth hormone, SV40, lacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-animal cells. The vector may further comprise nucleic acid sequences encoding for secretion signals. Such sequences are well known to the person skilled in the art. Furthermore, depending on the expression system used, leader sequences capable of directing e.g. an expressed polypeptide to a cellular compartment may be added to the coding sequence of the nucleic acid molecules and are well known in the art. The leader sequence(s) is (are) assembled in appropriate phase with translation, initiation and termination sequences.

Optionally, the heterologous sequence can encode a fusion protein including a C- or N-terminal identification peptide imparting desired characteristics, e. g., stabilization or simplified purification of expressed recombinant product. Once the vector has been incorporated into the appropriate host, the host is maintained under conditions suitable for high level expression of the nucleotide sequences, and, as desired, the collection and purification of the molecules such as proteins or fusion proteins of the invention may follow. Of course, the vector can also comprise regulatory regions from pathogenic organisms.

Furthermore, said vector may also be, besides an expression vector, a gene transfer and/or gene targeting vector. Gene therapy, which is based on introducing therapeutic genes (for example for vaccination) into cells by ex-vivo or in-vivo techniques is one of the most important applications of gene transfer. Suitable vectors, vector systems and methods for in-vitro or in-vivo gene therapy are described in the literature and are known to the person skilled in the art. The vectors and nucleic acids as described herein above may be designed for direct introduction or for introduction via liposomes, or viral vectors (e. g. adenoviral, retroviral) into the cell. Additionally, baculoviral systems or systems based on vaccinia virus or Semliki Forest Virus can be used as eukaryotic expression system according to the third aspect of the invention.

In a preferred embodiment of the invention the nucleic acid encodes a secretory form of the protein or a fragment hereof. In a preferred embodiment the secretory form lacks transmembrane domains.

As mentioned before, it is also envisaged that the protein encoded by the nucleic acid to be introduced in the cell line according to the second aspect of the present invention is glycosylated.

In accordance with the present invention the term culturing said host cell under conditions which permit the production of said molecule, e.g. a protein, means that the host cell of the invention comprising at least one nucleic acid encoding a protein molecule, preferably the preferred embodiments of said nucleic acid of the invention described elsewhere herein, is cultured under culture conditions which allow the expression of the protein molecule, e.g. in form of a protein molecule composition, preferably by secretion into the medium, preferably with high yields and/or high activity and/or high homogeneity as described elsewhere herein. Those skilled in the art are able to select the most suitable culture conditions by using suitable media and culture conditions such as but not limited to suitable time, temperature, pH, gasing, feed, medium, medium supplements, vessel or reactor sizes and principles known to those skilled in the art. Those skilled in the art are able to select and optimize the most suitable conditions. Preferred embodiments are described in the accompanying examples but are not limited to those.

Culturing of the cells can be carried out by any of general culturing methods for animal cells capable of efficiently producing the desired protein molecule composition, for example, batch culture, repeated batch culture, fed-batch culture and perfusion culture. Preferably, fed-batch culture or perfusion culture is employed in order to raise the productivity of the desired polypeptides.

In a further preferred embodiment of the invention said culturing is performed under serum-free conditions and/or animal component free condition.

In general, the molecules to be obtained according to the third aspect of the present invention can be purified by suitable fractionation techniques. The techniques for fractionations and purification steps are well known to those skilled in the art. The molecules can be obtained from the culturing media, for example as secreted molecules, or by preparation from cells, for example from membranes, cytoplasm, nucleoplasm or compartments like the endoplasmatic reticulum/golgi apparatus.

In one preferred embodiment the protein molecule composition is isolated by separating the media after culturing from the cells and/or cell debris for example by centrifugation techniques.

In a further preferred embodiment of the invention a protein molecule composition of the invention is isolated or further enriched by ultrafiltration, precipitation methods or other concentration methods known to those skilled in the art.

In a further preferred embodiment of the invention a protein molecule composition of the invention is isolated by purification of the protein molecule composition by chromatographic methods such as but not limited to affinity chromatography using according affinity materials such as but not limited to Protein A, Protein G, anti-antibody isotype antibodies, lectin chromatography, antibodies against a certain tag introduced into the protein molecule such as HIS-tag or myc-tag, or antigen, or by ion exchange chromatography known to those skilled in the art.

Further methods of purifying or enriching proteins or certain glycoforms of proteins are known to those skilled in the art and can be selected, adopted, optimized and used alone or in combination with the afore described methods by those skilled in the art to isolate or further purify, fractionate or enrich the protein molecule composition or fractions thereof of the invention.

In another preferred embodiment of the invention a protein molecule composition of the invention enriched in certain glycoforms of the protein molecule is isolated by lectin affinity chromatography with or without prior ultracentrifugation. Further methods of purifying or enriching proteins or certain glycoforms of proteins are known to those skilled in the art and can be selected, adopted, optimized and used alone or in combination with afore described methods by those skilled in the art to isolate or further purify, fractionate or enrich the protein molecule composition or fractions thereof of the invention.

In a fourth aspect, the present invention relates to a protein, or generally to a molecule, obtainable according to the third aspect of the present invention, i.e. by a method of producing a protein in a host cell, comprising the steps of:

a) introducing at least one nucleic acid encoding said protein in a cell as described in the context of the second aspect of the present invention;
b) culturing said host cell under conditions which permit the production of said protein; thereby producing the protein.

Said protein or molecule can be used for any purpose. However, it is especially preferred that the protein or molecule is useful as a medicament. An exemplary protein in this respect is the clotting factor FVII. FVII deficiency in subjects presents in a clinical setting as a hemophilia-like bleeding disorder. For example, recombinant FVII is used in treatment of hemophilia in a subgroup of hemophilia patients having developed inhibitors of replacement coagulation factor.

Protein molecule compositions of the fourth aspect of the present invention can be used for prophylactic and/or therapeutic treatment of diseases, such as leukemia, neutropenia, cytopenia, cancer, bone marrow transplantation, diseases of hematopoietic systems, infertility and autoimmune diseases. For example, G-CSF is an important therapeutic to treat neutropenia, a life-threatening decrease in neutrophils as consequence of a chemotherapy of leukemic cancer patients. GM-CSF is specifically used for treatment of AML patients at relative high age after chemotherapy to achieve a fast recovery from neutropenia. GM-CSF is additionally approved as therapeutic for several applications in bone marrow transplantations and for mobilization of peripheral blood stem cells. In addition, there are several clinical applications of GM-CSF that are currently under investigation, such as for treatment of HIV and cancer. Certain diseases of the hematopoietic system are treated with EPO, and IFN-beta is currently an important therapeutic for treatment of multiple sclerosis, an autoimmune disease. Another example is FSH which is widely used for treatment of male and female infertility. hCG is also applied for the treatment of infertility, but focusing on the anovulation in women. hGH has clinically-proven benefits, such as body fat reduction and muscle tissue increase.

Protein molecule compositions of the present invention can also be used for the manufacture of a medicament for prophylactic and/or therapeutic treatments of diseases selected from the group comprising leukemia, neutropenia, cytopenia, cancer, bone marrow transplantation, diseases of hematopoietic systems, infertility and autoimmune diseases.

The proteins or molecules according to the fourth aspect of the present invention can also be provided in the form of a pharmaceutical composition. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

In one embodiment, the composition is formulated in accordance with routine procedures as a pharmaceutical composition adapted for intravenous administration to human beings. Typically, compositions for intravenous administration are solutions in sterile isotonic aqueous buffer. In a preferred embodiment, the pharmaceutical compositions are in a water-soluble form, such as pharmaceutical acceptable salts, which is meant to include both acid and base addition salts. The administration of the candidate agents of the present invention can be done in a variety of ways, including, but not limited to, orally, subcutaneously, intravenously, intranasally, transdermally, intranodally, peritumourally, intratumourally, intrarectally, intraperitoneally, intramuscularly, intrapulmonary, vaginally, rectally, or intraocularly. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

A subject for the purposes of the present invention includes both humans and other animals, preferably vertebrates and more preferably mammals. Thus the methods are applicable to both human therapy and veterinary applications. In a preferred embodiment the subject is a mammal, e.g. a mouse, and in a most preferred embodiment the subject is human.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

Any statements made in the context of a specific aspect of the present invention are also applicable to the other aspects of the invention.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

Any recited exemplary methods herein are not to be construed to limit the scope of the invention. Specific examples are given in the Examples section accompanying the description.

The Examples illustrate the invention:

EXAMPLES

Cell Lines and Cell Culture

Throughout the examples, the NM-H9D8 cell line (also denoted as H9D8),. The NM-H9D8 cell line is deposited with the Deutsche Sammlung für Mikroorganismen and Zellkulturen GmbH ("DSMZ") having the deposit number DSM ACC 2806 and is described in detail in WO 2008/028686 A1.

The recombinant human factor VII expressing single cell clone FVII-H9D8-P1004-A2 (abbreviated as FVII-H9D8) was generated by stable transfection of NM-H9D8 with an expression construct harboring the proprotein of human factor VII (UniProt accession number P08709) for secretory production. In detail, to express the recombinant human factor VII in a NM-H9D8, cells were transfected with a vector coding for the recombinant human factor VII and the dhfr resistance gene by nucleofection. Two days post-transfection, growth medium was changed to selection medium (X-Vivo-20; 25 nM methotrexate) for 2 weeks. Clones were amplified by increasing methotrexate concentration to 50 nM and 100 nM. In this manner 3 rounds of gene amplification (25, 50, 100 nM methotrexate) were performed.

Following single cell cloning in 96-well plates by limited dilution (1 cell per well), plates were cultivated for 2 to 3 weeks. Growing cell clones were screened for productivity and good producing clones were selected for further gene amplification (200 nM methotrexate) and subsequent rounds of single cell cloning by limited dilution. The individual colonies were transferred to a 96-well plate, cultivated and expanded in selection medium (X-Vivo-20, 200 nM methotrexate) for analysis. As final single cell clone FVII-H9D8-P1004-A2 was identified.

The FVII-H9D8 clone was further modified by introducing a nucleic acid encoding ST6GAL1, thereby generating FVII-H9D8-P1004-A2-ST6 (abbreviated as FVII-H9D8-ST6). In detail, to express the sialyltransferase the cells were transfected with a vector coding for ST6GAL1 and the puromycin resistance gene by nucleofection. Two days post-transfection, growth medium was changed to selection medium (medium containing 0.5 μg/ml puromycin) for 2 weeks. Clones were isolated by limited dilution.

ST6GAL1 (NCBI Gene ID: 6480; updated on 5 Jun. 2016) encodes Beta-Galactosamide Alpha-2,6-Sialyltranferase 1. ST6GAL1 is a type II membrane protein that catalyzes the transfer of sialic acid from CMP-sialic acid to galactose-containing substrates. Three transcript variants encoding two different isoforms have been described. Important paralogs of this gene are ST6GAL2, ST6GALNAC4, ST6GALNAC5, ST6GALNAC3, ST6GALNAC6.

Assay for Determining Allele Frequency of B4GALNT3 and B4GALNT4 in H9D8

The determination of allele frequencies was performed by Sequencing Unit at Alacris Theranostics GmbH. Chromosome copy numbers were inferred from the WGS data comparing the read coverage between the test sample and the corresponding reference genome. The results are represented graphically in FIG. 1 and FIG. 2. Copy numbers are given from 0N (homozygous loss) to 4N and >4N for any copy number higher than 4N.

The allele frequency of B4GALNT3 and B4GALNT4 in H9D8 was determined using the graphical results. The genomic location for B4GALNT3 was identified as cytogenetic band: 12p13.33 and matched with the respective results and allele frequencies for chromosome 12. Copy numbers for B4GALNT3 were estimated as 3n. The genomic location for B4GALNT4 was identified as cytogenetic band: 11p15.5 and matched with the respective results and allele frequencies for chromosome 11. Copy numbers for B4GALNT3 were estimated as >4n.

Target Site Design and Construction of sgRNA Plasmids

The H9D8 subclone H9D8-2E2-3B11-P679-G6 and FVII-H9D8-5T6 were targeted in four loci: B4GALNT3 was targeted in exons 6 and 10, and B4GALNT4 was targeted in exons 4 to 6.

Target sites for CRISPR/Cas were designed using CRISPR gRNA Design tool of dna2.0. In detail described here for B4GALNT3 Exon 6 targeting gRNAs: Use CRISPR gRNA Design tool and choose Design my gRNA. Select as Species Homo sapiens, as PAM NGG and Nickase. gRNA offset was unchanged. Precede with Target a gene. Paste the Gene Name and select Search only in the first common exon. Confirm your settings and click search. The database recommends gRNAs. Select one gRNA sequence. The design of all other gRNAs was conducted accordingly.

gRNAs were constructed referring to addgenes gRNA Synthesis Protocol Option A. The gRNA expression constructs, so called gBlocks, were synthesized at GeneArt™ Gene Synthesis. For transfection and gRNA expression gBlocks were subcloned into an empty vector pCR-2.1-TOPO from Invitrogen.

The following gRNA plasmids were generated (only the sequences relevant for CRISPR/Cas are shown, each sequence comprising a U6 Promoter, a targeting sequence/crRNA coding sequence, a gRNA scaffold and a terminator;

for details refer to the additional information set forth in the accompanying sequence listing):

1. B4GALNT3 gRNA plasmids

B4GALNT3_Exon6_1(+) (SEQ ID NO: 9):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
ATTGCTGCAGATGACAACGTTTTAGAGCTAGAAATAGCAAGTTAAAATA
AGGCTAGTCCGTTATCAACTTGAAAAAGTGGCACCGAGTCGGTGCTTTTT
T

B4GALNT3_Exon6_1(-) (SEQ ID NO: 10):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
TGGATTTTCCCTGGGCAGCGTTTTAGAGCTAGAAATAGCAAGTTAAAATA
AGGCTAGTCCGTTATCAACTTGAAAAAGTGGCACCGAGTCGGTGCTTTTT
T

B4GALNT3_Exon10_2(+) (SEQ ID NO: 11):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
CCCGGGACACCCTCTATCGGTTTTAGAGCTAGAAATAGCAAGTTAAAATA
AGGCTAGTCCGTTATCAACTTGAAAAAGTGGCACCGAGTCGGTGCTTTTT
T

B4GALNT3_Exon10_2(-) (SEQ ID NO: 12):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
GCCGAAGCATGTCAGCGGGGTTTTAGAGCTAGAAATAGCAAGTTAAAATA
AGGCTAGTCCGTTATCAACTTGAAAAAGTGGCACCGAGTCGGTGCTTTTT
T

2. B4GALNT4 gRNA plasmids

B4GALNT4_Exon7_1(+) (SEQ ID NO: 13):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT

-continued

TTAAAATTATGTTTTAAAATGGACTATCATATGCTTACCGTAACTTGAAA
GTATTTCGATTTCTTGGCTTTATATATCTTGTGGAAAGGACGAAACACCG
GCGTGCACTTGTGTATTCGGTTTTAGAGCTAGAAATAGCAAGTTAAAATA
AGGCTAGTCCGTTATCAACTTGAAAAAGTGGCACCGAGTCGGTGCTTTTT
T

B4GALNT4_Exon7_1(-) (SEQ ID NO: 14):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
CCACAGTCACTCACCGCCTGTTTTAGAGCTAGAAATAGCAAGTTAAAATA
AGGCTAGTCCGTTATCAACTTGAAAAAGTGGCACCGAGTCGGTGCTTTTT
T

B4GALNT4_Exon4-6_2(+) (SEQ ID NO: 15):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
GGTTTCATCCACCCGGCGAGTTTTAGAGCTAGAAATAGCAAGTTAAAATA
AGGCTAGTCCGTTATCAACTTGAAAAAGTGGCACCGAGTCGGTGCTTTTT
T

B4GALNT4_Exon4-6_2(-) (SEQ ID NO: 16):

GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
AGTCCATAGTTCTTCCACTGTTTTAGAGCTAGAAATAGCAAGTTAAAATA
AGGCTAGTCCGTTATCAACTTGAAAAAGTGGCACCGAGTCGGTGCTTTTT
T

Stable Transfection Via Nucleofection

Cas9-D19A Nickase Plasmid was purchased from Sigma.

The day before transfection, 2·10^5 viable cells/ml were seeded. On the day of transfection, 2·10^6 cells were centrifuged for 5 min. at 1200 rpm in a 50 ml Falcon tube. The supernatant was decanted and the pellet was resuspended in 100 μl pre-warmed NFS solution consisting of 1 volume Supplement 1 and 4.5 equals of Nucleofector™ solution V. After addition of in total 25 μg linearized DNA in all (5 μg Cas9-D19A Nickase plasmid and each 2.5 μg of gRNA expression plasmid) the mixture was transferred to a cuvette and electroporated with the respective program of the Amaxa™ system. Subsequently, 500 μl pre-warmed medium was pipetted immediately in the cuvette and the whole content was transferred in a 6-well plate containing 2 ml medium. The transfected cells were diluted after one day when needed and seeded in selection medium after the second day.

Single Cell Cloning

To obtain a genetically uniform cell population, the cells were cloned by limited dilution from the pool.

Genotypic Analyses of Isolated Clones

Generated pools of clones were analyzed by T7EI assay, in vitro Cas9 assay and Deep Amplicon Sequencing. In each step, a preselection of clones for the consecutive step was made in order to minimize screening efforts.

The in vitro Cas9 assay is described above. A more detailed protocol is available, e.g., from the Guide-it Genotype Confirmation Kit (Clontech, #632611). Briefly, the gRNA transfection plasmids were translated in gRNAs by PCR amplification with special primers including T7 promoter at 5' end in the first step and subsequent treatment with T7 RNA polymerase. Genomic DNA of single cell clones was extracted and the modified loci were amplified by PCR. The resulting fragments were treated with a Cas9/sgRNA mix for two hours and the samples were analyzed by gel electrophoresis.

For Deep Amplicon Sequencing, genomic DNA of potentially modified clones was extracted and mutations were analyzed by Deep Amplicon Sequencing performed by Microsynth. Therefor the four modified loci were amplified by PCR in several steps and sequenced by paired-end run with the Illumina platform. The sequencing reads were trimmed, merged, dereplicated and filtered to obtain comprehensive read cluster. In order to detect mutations the resulting data were aligned against the hg38 reference genome.

The results of the sequenced clones were analyzed in Vector NTI by alignment of each locus against H9D8-2E2-3B11-P679-G6 which was included in the pool of sequenced clones. Several possible gene variants were obtained by combination of different mutations per locus (two per gene) and the likelihood of occurrence was determined based on the frequency of reads containing the corresponding mutation. For each gene variant the open reading frame as well as the resulting protein was predicted for each clone.

Genetic Modification of B4GALNT3 and B4GALNT4 in H9D8 (Individually and in Combination)

Genomic DNA of 41 potential B4GALNT3 mutant clones was isolated and analyzed by T7EI assay to determine genome targeting efficiency. The results indicate that 10 clones are mutated in both targeted loci of B4GALNT3 gene, 18 clones in one of two targeted loci of B4GALNT3 and for 13 clones gene editing of B4GALNT3 could not be proven. 3 most promising clones of 10 were analyzed by in vitro Cas9 assay to verify the results and to determine if a given clone has solely mutated alleles, a mix of mutated and wildtype alleles or has solely unchanged alleles (wild type). For all three clones positive results were obtained and clones were analyzed by NGS to verify mutations.

In one out of three clones Deep Amplicon Sequencing analyses confirmed mutations in all alleles for both targeted loci of B4GALNT3 gene resulting in frame shifts of the open reading frame which lead to a premature termination codon (P1126-E7). In two out of three clones Deep Amplicon Sequencing analyses confirmed a partial targeting of one of two loci with the chance for at least one not mutated allele but mutations in all alleles of the second locus of B4GALNT3 gene resulting in a frame shift of the open reading frame which lead to a premature termination codon (P1126-A7 and G6). In all three clones targeting was successful achieving B4GALNT3 deficient cells.

Genomic DNA of 39 potential B4GALNT4 mutant clones was isolated and analyzed by T7EI assay to determine genome targeting efficiency. The results indicate that 7 clones are mutated in both targeted loci of B4GALNT4, 19 clones in one of two targeted loci of B4GALNT4 and for 13 clones gene editing of B4GALNT4 could not be proven. 3 most promising clones of 7 were analyzed by in vitro Cas9 assay to verify the results and to determine if a given clone has solely mutated alleles, a mix of mutated and wildtype alleles or has solely unchanged alleles (wild type). For all three clones positive results were obtained and clones were analyzed by NGS to verify mutations.

In one out of three clones Deep Amplicon Sequencing analyses confirmed mutations in all alleles for both targeted loci of B4GALNT4 gene resulting in frame shifts of the open reading frame which did not lead to a premature termination codon but to an altered protein sequence with unknown functionality (P1127-B4). In two out of three clones Deep Amplicon Sequencing analyses confirmed mutations in all alleles of the second locus of B4GALNT4 gene resulting in frame shifts of the open reading frame which lead to a premature termination codon (P1127-F8 und H3). In two clones targeting was successful achieving B4GALNT4 deficient cells.

For the analysis of potential B4GALNT3+4 mutant clones (genetic modification of B4GALNT3 and B4GALNT4 in combination) genomic DNA of 36 clones was isolated and analyzed by T7EI assay to determine genome targeting efficiency. The results indicate that 17 clones are mutated in at least one locus of both targeted genes, at least one locus of B4GALNT3 and at least one locus of B4GALNT4, 3 clones are mutated in both loci of either B4GALNT3 or B4GALNT4 and 13 clones in only one locus of one targeted gene, either one locus of B4GALNT3 or one locus of B4GALNT4. For 3 clones gene editing of B4GALNT3+4 was not successful. 5 most promising clones of 17 were analyzed by in vitro Cas9 assay to verify the results and to determine if a given clone has solely mutated alleles, a mix of mutated and wildtype alleles or has solely unchanged alleles (wild type). For four out of five clones positive results were obtained and clones were analyzed by NGS to verify mutations.

In one out of four clones Deep Amplicon Sequencing analyses confirmed for one of two loci (second locus) of B4GALNT3 gene a partial targeting with the chance for at least one not mutated allele. Deep Amplicon Sequencing analyses confirmed partial targeting of one locus of B4GALNT4 gene with the chance for at least one not mutated allele and mutations in all alleles of the second locus of B4GALNT4 gene resulting in a frame shift of the open reading frame which lead to a premature termination codon (P1128-D9 KO only for B4GALNT4 and altered protein sequence with unknown functionality for B4GALNT3). In two out of four clones Deep Amplicon Sequencing analyses confirmed partial targeting for both loci of B4GALNT3 and B4GALNT4 (P1128-A5 und E5). For one of four clones Deep Amplicon Sequencing failed and no results were obtained (P1128-B5). In none of the analyzed three clones targeting was successful achieving B4GALNT3+4 deficient cells but cells expressing altered protein sequences with unknown functionality.

To boost the chance for obtaining a B4GALNT3+4 mutant the most promising clone was chosen for a second round of transfection with CRISPR/Cas9. For the analysis of potential B4GALNT3+4 mutant clones after two rounds of CRISPR/Cas9 genomic DNA of 65 clones was isolated and analyzed by T7EI assay to determine genome targeting efficiency. The results indicate that 25 clones are mutated in at least one locus of both targeted genes, at least one locus of B4GALNT3 and at least one locus of B4GALNT4, 1clone is mutated in both loci of B4GALNT3 and 21 clones in only one locus of one targeted gene, either one locus of B4GALNT3 or one locus of B4GALNT4. For 18 clones gene editing of B4GALNT3+4 was not successful. 6 most promising clones of 25 were analyzed by in vitro Cas9 assay to verify the results and to determine if a given clone has solely mutated alleles, a mix of mutated and wildtype alleles or has solely unchanged alleles (wild type). For five out of six clones positive results were obtained and clones were analyzed by NGS to verify mutations.

In two out of five clones Deep Amplicon Sequencing analyses confirmed mutations in all alleles for both targeted loci of B4GALNT3 gene resulting in frame shifts of the open reading frame which lead to a premature termination codon. Deep Amplicon Sequencing analyses confirmed mutations in all alleles for the first targeted locus of B4GALNT4 gene resulting in an altered protein sequence with unknown functionality (P1172-A4 and D12 KO only in B4GALNT3 and altered protein sequence with unknown functionality for B4GALNT4).

In one out of five clones Deep Amplicon Sequencing analyses confirmed for the first locus of B4GALNT3 gene mutations in all alleles resulting in an altered protein sequence with unknown functionality and mutations in all alleles of the second targeted locus of B4GALNT3 gene resulting in a frame shift of the open reading frame which lead to a premature termination codon. Deep Amplicon Sequencing analyses confirmed mutations in all alleles for the first targeted locus of B4GALNT4 gene resulting in an altered protein sequence with unknown functionality (P1172-C2 KO only in B4GALNT3 and altered protein sequence with unknown functionality for B4GALNT4). In one out of five clones Deep Amplicon Sequencing analyses confirmed for both loci of B4GALNT3 gene mutations in all alleles resulting in an altered protein sequence with unknown functionality. Deep Amplicon Sequencing analyses confirmed mutations in all alleles for the first targeted locus of B4GALNT4 gene resulting in a frame shift of the open reading frame which lead to a premature termination codon (P1172-D8 KO only in B4GALNT4 and altered protein sequence with unknown functionality for B4GALNT3).

In one out of five clones Deep Amplicon Sequencing analyses confirmed mutations in all alleles for the first locus of B4GALNT3 gene resulting in a frame shift of the open reading frame which lead to a premature termination codon and mutations in all alleles for the second targeted locus of B4GALNT3 gene resulting in an altered protein sequence with unknown functionality. Deep Amplicon Sequencing analyses confirmed mutations in all alleles for the first targeted locus of B4GALNT4 gene resulting in a frame shift of the open reading frame which lead to a premature termination codon (P1172-H8 KO in B4GALNT3 & 4).

In one of the analyzed five clones targeting was successful achieving B4GALNT3+4 deficient cells.

Genetic Modification of B4GALNT3+4 in FVII-H9D8-ST6

For the analysis of potential B4GALNT3+4 mutant clones genomic DNA of 21 clones was isolated and analyzed by T7EI assay to determine genome targeting efficiency. The results indicate that 3 clones are mutated in at least one locus of both targeted genes, at least one locus of B4GALNT3 and at least one locus of B4GALNT4, 1 clone is mutated in both loci of either B4GALNT3 or B4GALNT4 and 6 clones in only one locus of one targeted gene, either one locus of B4GALNT3 or one locus of B4GALNT4. For 11 clones gene editing of B4GALNT3+4 was not successful. 1 most promising clone of 3 was analyzed by in vitro Cas9 assay to verify the results and to determine if a given clone has solely mutated alleles, a mix of mutated and wildtype alleles or has solely unchanged alleles (wild type). For one out of one clones positive results were obtained and the clone was analyzed by NGS to verify mutations. In one out of one clones Deep Amplicon Sequencing analyses confirmed for the second locus of B4GALNT3 gene mutations in all alleles resulting in either a frame shift of the open reading frame which lead to a premature termination codon or at a low percentage in an altered protein sequence with unknown functionality. Deep Amplicon Sequencing analyses confirmed mutations in all alleles for both targeted loci of B4GALNT4 gene resulting in a frame shift of the open reading frame which lead to a premature termination codon (P1130-A7 KO in B4GALNT4 and 3 with small chance of altered protein sequence with unknown functionality for B4GALNT3). In one analyzed clone targeting was successful achieving B4GALNT3+4 deficient cells.

To boost the chance for a double knockout of B4GALNT3+4 one promising clone was chosen for a second round of transfection with CRISPR/Cas9. For the analysis of potential double knockout B4GALNT3+4 clones after two rounds of CRISPR/Cas9 genomic DNA of 8 clones was isolated and analyzed by T7EI assay to determine genome targeting efficiency. The results indicate that 2 clones are mutated in at least one locus of both targeted genes, at least one locus of B4GALNT3 and at least one locus of B4GALNT4, 2 clones are mutated in both loci of either B4GALNT3 or B4GALNT4 and 4 clones in only one locus of one targeted gene, either one locus of B4GALNT3 or one locus of B4GALNT4. Two clones were analyzed by NGS to verify mutations.

In one out of two clones Deep Amplicon Sequencing analyses confirmed for the second locus of B4GALNT3 gene mutations in all alleles resulting in either a frame shift of the open reading frame which lead to a premature termination codon or at a low percentage in an altered protein sequence with unknown functionality. Deep Amplicon Sequencing analyses confirmed mutations in all alleles for both targeted loci of B4GALNT4 gene resulting in a frame shift of the open reading frame which lead to a premature termination codon with the exception for at least one allele of the second locus of B4GALNT4 (P1181-B2 KO in B4GALNT4 and 3 with small chance of altered protein sequence with unknown functionality for B4GALNT3).

In one out of two clones Deep Amplicon Sequencing analyses confirmed mutations in all alleles of the second locus of B4GALNT3 gene resulting in a frame shift of the open reading frame which lead to a premature termination codon. (P1181-A4 KO only in B4GALNT3). In one of the analyzed two clones targeting was successful achieving B4GALNT3+4 deficient cells.

Exemplary Detailed Results for B4GALNT3+4 in H9D8

1st CRISPR round:

no clone with complete K.O. in B4GALNT3 Exon6

2 out of 3 clones with complete K.O. in B4GALNT3 Exon10, but no clone with complete frameshift-mutation 2 out of 3 clones with complete K.O. in B4GALNT4 Exon5, 1 out of them with unpredictable large exon deletion 2 out of 3 clones with complete K.O. in B4GALNT4 Exon7, 1 out of them with unpredictable large exon deletion All in all: only heterozygous B4GALNT3 K.O. clones, 2 out of them with heterozygous B4GALNT4 K.O., 1 out of them with homozygous B4GALNT4 K.O.

2nd CRISPR round:

all clones with complete K.O. in B4GALNT3 Exon6, 3 out of them with frameshift-mutation all clones with complete K.O. in B4GALNT3 Exon10, 3 out of them with frameshift-mutation all clones with complete K.O. in B4GALNT4 Exon5, 2 out of them with frameshift-mutation all clones with complete K.O. in B4GALNT4 Exon7, 2 out of them with frameshift-mutation All in all: no clones without mutation in B4GALNT3 and 4, 4 out of 5 with homozygous B4GALNT3 K.O., 1 out of them with homozygous B4GALNT4 K.O., too

| | GALNT3 | | GALNT4 | |
|---|---|---|---|---|
| | Exon 6 | Exon 10 | Exon 5 | Exon 7 |
| GalNT 3-KO | 23 bp Ins | 23 bp Del | wt | wt |
| GalNT 4-KO | wt | wt | 55 bp Del | wt |
| GalNT 3 + 4-KO (2nd CRISPR) | 7 bp Del + 13 bp Del 5 bp Ins | 6 bp Ins 4 bp Del + 34 bp Del | 33 bp Del with PTC | wt |
| GalNT 3 + 4-KO ST† (2nd CRISPR) | wt | 37 bp Del 27 bp Del | 7 bp Del | complete deletion of Exons 6 and 7 |

Phenotypic Analysis of Isolated Clones

Recombinant FVII was purified from FVII-H9D8 and FVII-H9D8-ST6 and from a corresponding B4GALNT3+4 mutant clone. The obtained FVII samples were analyzed by N-Glycan Profiling.

Recombinant Expression and Purification of FVII

Factor VII was purified directly from cell culture supernatant of transfected cells using one chromatography step by affinity chromatography, resulting in a pure composition of the γ-carboxylated polypeptide FVII. The affinity chromatography is usually performed by equilibrating and loading the column, followed by a wash and subsequent elution, each with a buffer preferably adapted to the binding conditions of the immobilized antibody. The equilibration, load and wash are carried out by using a mobile phase buffering at neutral pH, The γ-carboxylated polypeptide is eluted from the affinity chromatography matrix using an elution buffer with an acidic pH in the range of from 2.0 to 4.0. The composition comprising the γ-carboxylated polypeptide preferably is neutralized to a pH in the range of from 6.5 to 9.5.

N-Glycan Profiling

Sample preparation is based on the Rapiflour labeling kit (Waters Inc. Milford USA). Briefly, 15 μg of the glycoprotein is denatured with RapiGest SF (6 μL) and 6.5 μL of 4 mM tris(2-carboxyethyl)phosphine at 95° C. for 2 h. N-Glycan release is performed with 1.2 μL of Rapid PNGase F solution at 55° C. for 10 min followed by fluorescence tagging of free N-glycans with the RapiFluor labeling reagent (1.2 μL, 23 mg reagent in 335 μL dimethyl formamide) for 10 min at 55° C. The reaction is terminated by addition of 358 μL of acetonitrile. Samples are purified by use of a HILIC pElution plate. Loaded samples are washed with two times 600 μL of formic acid/water/acetonitrile (1:9:90 v/v/v). Fluorescence tagged N-glycans are eluted with 3×30 μL of GlycoWorks SPE elution buffer. Samples are dried, re-dissolved in 15 μL of 100 mM ammonium formate pH 4.5/acetonitrile (40:60 v/v), 5 μL of the solution are applied to separation by HILIC-UPLC with fluorescence detection: Waters I-Class chromatography instrument, Acquity Glycan BEH column (150×2.1 mm), Gradient: 22 to 44% 100 mM ammonium formate pH 4.5, Flow rate: 0.5 mL/min. Structure identification is based on ultra-high resolution ESI-QToF mass spectrometry (MSMS). Results of N-glycan profiling are shown in FIG. 1.

Small-scale bioreactor evaluation of three GEX® clones (SAM-AMBR): 1. FVII-H9D8 P1004-A2 (WT/Ref), 2. FVII-P1172-H8 pool (GNT 3/4 Ko) and 3. FVII-H9D8 P1004-A2 ST6 GalNAC KO P1130-A7 (ST6-oe+GNT3/4 KO)

Microbioreactor cultivations were performed in the ambr™ (advanced mircobioreactor) system (TAP Biosystems/Sartorius). Each spargeless vessel was individually supplied with nitrogen (or air), oxygen (to maintain DO), carbon dioxide (to decrease pH) or a mix of these gases. For each cell line duplicate reactors were run.

All three cell lines (FVII-H9D8 P1004-A2, FVII-P1172-H8 pool and FVII-H9D8 P1004-A2 ST6 GalNAC KO P1130-A7) were inoculated with $5\times10^5$ cells/ml in GTM 1× medium in a total working volume of 15 ml per vessel. Cultivation was performed at 37° C., 40% DO and vessels were stirred with 830 rpm. Maintenance of pH was assured by addition of 0.5 M NaOH and by supplying $CO_2$; pH was calibrated every 3-4 days by offline measurements. Samples for cell concentration and metabolite measurement were taken daily by the programmable liquid handler. Perfusion (as described in WO2016193083 A1) was initiated on day 2 by removal of 3 mL of the culture (harvest) by the liquid handler. For a perfusion rate of one reactor volume ($V_r$/d) four "removal steps" are necessary per day. On day 7, GTM 1× feed medium was replaced stepwise with enriched GTM 2× medium. The daily harvests were collected in 24-deep wells plates. Three supernatant harvest pools were generated and product concentration was determined by Octet (Pall/Fortebio):

Pool 1 culture days 3-9 (early harvest)

Pool 2 culture days 10-16 (mid harvest)

Pool 3 culture days 17-23 (late harvest)

In addition, on days 9, 16 and 23, cells (~2×10^6) were removed from the running culture in order to perform mRNA extraction (Nucleo spin RNA plus kit—Macherey-Nagel) and qPCR analysis (Lightcycler) using a standard method.

For the purpose of N-glycan analysis the supernatant was purified by on step VII-Select chromatography (GE Healthcare). The sample was denaturered and the N-glycans were released by action of PNGase F and subsequently fluorescence tagged with RapiFluor® (Waters). The N-glycan profile was recorded by use of HILIC-UPLC-FLD. The following conditions were applied: flow rate 0.5 mL/min, oven temperature 60° C., solvent A=acetonitrile, solvent B=100 mM Ammoniumformiat-Puffer pH 4.5, gradient 22-44%B within 85 min, fluorescence excitation 265 nm, fluorescence emission 425 nm. Quantification of N-glycans is based on fluorescence signals. For structure identification online coupled high resolution ESI-QTOF MS/MS is used. The following settings were used for ESI-QTOF MS/MS (Compact, Bruker):

| Method: | |
|---|---|
| Scan Begin | 80 m/z |
| Scan End | 2800 m/z |
| Ion Polarity | Positive |
| Source | |
| Set End Plate Offset | (−)500 V |
| Set Capillary | 4500 V |
| MS/MS | |
| Precursor Ion List | Exclude 20.00-500.00<br>Exclude 1800.00-40000.00<br>Include 500-1800 |

-continued

| Tune | |
|---|---|
| Set Funnel 1RF | 400 Vpp |
| Set Funnel 2RF | 400 Vpp |
| Hexapole RF | 400 Vpp |
| Quadrupole Ion Energy | 4 eV |
| Low Mass | 500 m/z |
| Collision Energy | 7 eV |
| PrePulse Storage | 10 µs |
| Collision Cell RF | 2500 Vpp |
| Set Transfer Time | 120 µs |

Results

For all three cell lines, overall growth and basic metabolism were similar. All cell lines grew at high viability (>90%) reaching maximal cell densities of about $15\times10^6$ cells/ml. For each cell line the productivity was stable over the entire duration of the cultivation. The cell lines FVII-H9D8 P1004-A2 and FVII-H8 pool differ in terms of productivity due to different level of amplification, which result in different productivity per cell and day. However, genetic modification of FVII-H9D8 P1004-A2, which leads to FVII-H9D8 P1004-A2 ST6 GalNAc KO P1130-A7 has no impact on productivity. mRNA analysis shows that upregulation of ST6 enzyme expression occurs and remains stable during the entire culture process. The glycananalysis reveals as well, that GalNAc is not present on N-Glycans of FVII when expressed in GalNAc-KO cells throughout the production process (FIG. 2).

The invention claimed is:

1. A method of modifying B4GALNT3 and B4GALNT4 in a cell via CRISPR/Cas, wherein the cell has at least three alleles of B4GALNt3 and has at least four alleles of B4GALNT4, and wherein modifying B4GALNT3 and B4GALNT4 via CRISPR/Cas eliminates GalNAc residues within N-gylcans in proteins expressed by the cell.

2. The method of claim 1, wherein all alleles of B4GALNT3 and B4GALNT are modified.

3. The method of claim 1, wherein B4GALNT3 and B4GALNT4 are targeted in at least one position of the nucleotide sequence of their coding and/or regulatory regions(s).

4. The method of claim 1, wherein modifying B4GALNT3 and B4GALNT4 via CRISPR/Cas has results in introduction of one or more insertion(s), deletion(s) and/or substitution(s) of one or more nucleotides or a combination thereof in a coding and/or regulatory region of B4GALNT3 and B4GALNT4.

5. The method of claim 1, wherein modifying B4GALNT4 via CRISPR/Cas results in decreased transcription and/or expression of B4GALNT3 and B4GALNT4 and/or in production of a variant of GalNT3 and GAlNT4 which is truncated and/or has altered enzymatic activity.

6. The method according to claim 1, wherein the cell is a human cell or is derived from a human cell.

7. The method according to claim 1, wherein the cell is an immortalized cell.

8. The method according to claim 3, wherein for each position to be targeted the CRISPR/Cas system comprises two gRNA plasmids, each gRNA plasmid comprising a specific targeting sequence.

9. The method according to claim 1, wherein B4GALNT3 and B4GALNT4 are each targeted in two positions.

10. The method according to claim 9, wherein the targeting sequences specific for B4GALNT3 are selected from the group consisting of ATTGCTGCAGATGACAACG (SEQ ID NO: 1)/TGGATTTTCCCTGGGCAGC (SEQ ID NO: 2) and CCCGGGACACCCTCTATCG (SEQ ID NO: 3)/GGCCGAAGCATGTCAGCGGG (SEQ ID NO: 4); and/or wherein the targeting sequences specific for B4GALNT4 are selected from GCGTGCACTTGTGTATTCG (SEQ ID NO: 5)/CCACAGTCACTCACCGCCT (SEQ ID NO: 6) and GGTTTCATCCACCCGGCGA (SEQ ID NO: 7)/GAGTCCATAGTTCTTCCACT (SEQ ID NO: 8).

11. The method of claim 1, wherein B4GALNT3 and B4GALNT4 are targeted in two positions of the nucleotide sequence of their coding and/or regulatory region(s).

* * * * *

SEQUENCE LISTING

```
<160> NUMBER OF SEQ ID NOS: 16

<210> SEQ ID NO 1
<211> LENGTH: 19
<212> TYPE: DNA
<213> ORGANISM: artificial
<220> FEATURE:
<223> OTHER INFORMATION: targeting sequence for B4GALNT3

<400> SEQUENCE: 1

attgctgcag atgacaacg                                                 19


<210> SEQ ID NO 2
<211> LENGTH: 19
<212> TYPE: DNA
<213> ORGANISM: artificial
<220> FEATURE:
<223> OTHER INFORMATION: targeting sequence for B4GALNT3

<400> SEQUENCE: 2

tggattttcc ctgggcagc                                                 19


<210> SEQ ID NO 3
<211> LENGTH: 19
<212> TYPE: DNA
<213> ORGANISM: artificial
<220> FEATURE:
<223> OTHER INFORMATION: targeting sequence for B4GALNT3

<400> SEQUENCE: 3

cccgggacac cctctatcg                                                 19
```

<210> SEQ ID NO 4
<211> LENGTH: 20
<212> TYPE: DNA
<213> ORGANISM: artificial
<220> FEATURE:
<223> OTHER INFORMATION: targeting sequence for B4GALNT3

<400> SEQUENCE: 4
ggccgaagca tgtcagcggg 20

<210> SEQ ID NO 5
<211> LENGTH: 19
<212> TYPE: DNA
<213> ORGANISM: artificial
<220> FEATURE:
<223> OTHER INFORMATION: targeting sequence for B4GALNT4

<400> SEQUENCE: 5
gcgtgcactt gtgtattcg 19

<210> SEQ ID NO 6
<211> LENGTH: 19
<212> TYPE: DNA
<213> ORGANISM: artificial
<220> FEATURE:
<223> OTHER INFORMATION: targeting sequence for B4GALNT4

<400> SEQUENCE: 6
ccacagtcac tcaccgcct 19

<210> SEQ ID NO 7
<211> LENGTH: 19
<212> TYPE: DNA
<213> ORGANISM: artificial
<220> FEATURE:
<223> OTHER INFORMATION: targeting sequence for B4GALNT4

<400> SEQUENCE: 7
ggtttcatcc acccggcga 19

<210> SEQ ID NO 8
<211> LENGTH: 20
<212> TYPE: DNA
<213> ORGANISM: artificial
<220> FEATURE:
<223> OTHER INFORMATION: targeting sequence for B4GALNT4

<400> SEQUENCE: 8
gagtccatag ttcttccact 20

<210> SEQ ID NO 9
<211> LENGTH: 351
<212> TYPE: DNA
<213> ORGANISM: artificial
<220> FEATURE:
<223> OTHER INFORMATION: B4GALNT3 gRNA plasmid Exon6 1(+)

<400> SEQUENCE: 9
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg attgctgcag atgacaacgg ttttagagct agaaatagca agttaaaata 300
aggctagtcc gttatcaact tgaaaaagtg gcaccgagtc ggtgcttttt t 351

<210> SEQ ID NO 10
<211> LENGTH: 351
<212> TYPE: DNA
<213> ORGANISM: artificial
<220> FEATURE:
<223> OTHER INFORMATION: B4GALNT3 gRNA plasmid Exon6 1(-)

<400> SEQUENCE: 10
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg tggattttcc ctgggcagcg ttttagagct agaaatagca agttaaaata 300
aggctagtcc gttatcaact tgaaaaagtg gcaccgagtc ggtgcttttt t 351

<210> SEQ ID NO 11
<211> LENGTH: 351
<212> TYPE: DNA
<213> ORGANISM: artificial
<220> FEATURE:
<223> OTHER INFORMATION: B4GALNT3 gRNA plasmid Exon10 2(+)

<400> SEQUENCE: 11
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg cccgggacac cctctatcgg ttttagagct agaaatagca agttaaaata 300
aggctagtcc gttatcaact tgaaaaagtg gcaccgagtc ggtgcttttt t 351

<210> SEQ ID NO 12
<211> LENGTH: 351
<212> TYPE: DNA
<213> ORGANISM: artificial
<220> FEATURE:
<223> OTHER INFORMATION: B4GALNT3 gRNA plasmid Exon10 2(-)

<400> SEQUENCE: 12
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg gccgaagcat gtcagcgggg ttttagagct agaaatagca agttaaaata 300
aggctagtcc gttatcaact tgaaaaagtg gcaccgagtc ggtgcttttt t 351

<210> SEQ ID NO 13
<211> LENGTH: 351
<212> TYPE: DNA
<213> ORGANISM: artificial
<220> FEATURE:
<223> OTHER INFORMATION: B4GALNT4 gRNA plasmid Exon7 1(+)

<400> SEQUENCE: 13
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg gcgtgcactt gtgtattcgg ttttagagct agaaatagca agttaaaata 300
aggctagtcc gttatcaact tgaaaaagtg gcaccgagtc ggtgcttttt t 351

<210> SEQ ID NO 14
<211> LENGTH: 351
<212> TYPE: DNA
<213> ORGANISM: artificial
<220> FEATURE:
<223> OTHER INFORMATION: B4GALNT4 gRNA plasmid Exon7 1(-)

<400> SEQUENCE: 14
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg ccacagtcac tcaccgcctg ttttagagct agaaatagca agttaaaata 300
aggctagtcc gttatcaact tgaaaaagtg gcaccgagtc ggtgcttttt t 351

<210> SEQ ID NO 15
<211> LENGTH: 351
<212> TYPE: DNA
<213> ORGANISM: artificial
<220> FEATURE:
<223> OTHER INFORMATION: B4GALNT4 gRNA plasmid Exon4-6 2(+)

<400> SEQUENCE: 15
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg ggtttcatcc acccggcgag ttttagagct agaaatagca agttaaaata 300
aggctagtcc gttatcaact tgaaaaagtg gcaccgagtc ggtgcttttt t 351

<210> SEQ ID NO 16
<211> LENGTH: 351
<212> TYPE: DNA
<213> ORGANISM: artificial
<220> FEATURE:
<223> OTHER INFORMATION: B4GALNT4 gRNA plasmid Exon4-6 2(-)

<400> SEQUENCE: 16
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg agtccatagt tcttccactg ttttagagct agaaatagca agttaaaata 300
aggctagtcc gttatcaact tgaaaaagtg gcaccgagtc ggtgcttttt t 351